United States Patent
Xie et al.

(10) Patent No.: US 10,670,615 B2
(45) Date of Patent: Jun. 2, 2020

(54) SYSTEMS AND METHODS FOR INTERFERENCE CORRECTION FROM HEMOGLOBIN VARIANTS

(71) Applicant: Polymer Technology Systems, Inc., Indianapolis, IN (US)

(72) Inventors: Charles Z. Xie, Indianapolis, IN (US); Jane Kyung, Indianapolis, IN (US); Tu-Anh Nguyen, Indianapolis, IN (US); Annie V. Mendoza, Indianapolis, IN (US); Keith Moskowitz, Indianapolis, IN (US)

(73) Assignee: Polymer Technology Systems, Inc., Whitestown, IN (US)

( * ) Notice: Subject to any disclaimer, the term of this patent is extended or adjusted under 35 U.S.C. 154(b) by 488 days.

(21) Appl. No.: 15/369,340

(22) Filed: Dec. 5, 2016

(65) Prior Publication Data

US 2017/0176464 A1    Jun. 22, 2017

Related U.S. Application Data

(60) Provisional application No. 62/263,478, filed on Dec. 4, 2015, provisional application No. 62/322,687, filed on Apr. 14, 2016.

(51) Int. Cl.
*G01N 33/558* (2006.01)
*G01N 33/72* (2006.01)
*G01N 33/543* (2006.01)

(52) U.S. Cl.
CPC ..... *G01N 33/723* (2013.01); *G01N 33/54313* (2013.01); *G01N 33/558* (2013.01); *G01N 33/726* (2013.01); *G01N 2333/805* (2013.01)

(58) Field of Classification Search
CPC .... G01N 33/53; G01N 33/525; G01N 33/558; G01N 33/585; G01N 33/587; G01N 33/54346; G01N 33/54386; G01N 2021/7759; G01N 2021/757; G01N 2021/7763; G01N 2035/00108
(Continued)

(56) References Cited

U.S. PATENT DOCUMENTS

| 7,470,548 B2 * | 12/2008 | Ozawa ............... A61L 9/014 436/518 |
| 2011/0091357 A1 | 4/2011 | Blatt et al. |
| 2014/0073532 A1 | 3/2014 | Walker et al. |

FOREIGN PATENT DOCUMENTS

EP    0185870 B2    6/1998

OTHER PUBLICATIONS

International Search Report and Written Opinion dated Feb. 16, 2017 issued in related PCT App. No. PCT/US2016/064967 (11 pages).

* cited by examiner

*Primary Examiner* — Christopher L Chin
(74) *Attorney, Agent, or Firm* — Haynes and Boone, LLP

(57) ABSTRACT

A system for determining a concentration of hemoglobin A1C includes a first lateral flow test strip, the first lateral flow test strip providing for a percent of HbA1C concentration; a second lateral flow test strip, the second lateral flow test strip providing for the total amount of hemoglobin; an antibody-microparticle stripe on each of the first and second lateral flow test strips; a conjugate stripe on each of the first and second lateral flow test strips; and a sample treatment buffer. The sample treatment buffer is strongly denaturing, and antibodies in the antibody-microparticle strip are covalently bound to microparticles.

12 Claims, 16 Drawing Sheets

(58) Field of Classification Search
USPC ......................................................... 436/514
See application file for complete search history.

Amount of methemoglobin formed with increasing sodium nitrite concentration.

SYSTEMS AND METHODS FOR INTERFERENCE CORRECTION FROM HEMOGLOBIN VARIANTS

CROSS-REFERENCES TO RELATED APPLICATIONS

This application claims the benefit of Provisional Application No. 62/263,478 filed on Dec. 4, 2015 titled "Systems and Methods For Interference Correction From Hemoglobin Variants" and of Provisional Application No. 62/322,687 filed on Apr. 14, 2016 titled "Systems and Methods For Interference Correction From Hemoglobin Variants."

BACKGROUND

Point of Care ("POC") and home testing for various blood analytes and other detectable metrics in bodily fluids is desirable for patient and doctor. One such analyte is A1C, a type of glycated hemoglobin. High levels of blood glucose cause over-glycation of proteins, including hemoglobin, throughout the body. Glycation of hemoglobin can occur at the amino termini of the alpha and beta chains, as well as other sites with free amino groups. Hemoglobin A undergoes a slow glycation with glucose that is dependent on the time-average concentration of glucose over the 120-day life span of red blood cells. The most prevalent and well-characterized species of glycated hemoglobin A is A1C, making up approximately 3% to 6% of the total hemoglobin in healthy individuals. The correlation of A1C and blood glucose levels make it a useful method of monitoring long-term blood glucose levels in people with diabetes. The mean (average) blood glucose level (MBG) is a function of the A1C levels and, therefore, is derivable.

Polymer Technology Systems, Inc. (PTS), manufactures the A1CNow®, a Point-of-Care device for measuring HbA1C. This test is an immunochemistry (antigen-antibody)-based system which performs well unless the patient has hemoglobin variances HbS and HbC which create false high results as much as 30%. It would be desirable to provide an assay that is not affected by these hemoglobin variances.

BRIEF SUMMARY

Provided herein are multiple methods for improving the performance of a system measuring HbA1C in respect to variants found in the population. In one embodiment, a system for determining a concentration of hemoglobin A1C includes a first lateral flow test strip, the first lateral flow test strip providing for a percent of HbA1C concentration and providing for the total amount of hemoglobin, an antibody-microparticle stripe on the first lateral flow test strip. The system further includes a conjugate stripe on the first lateral flow test strip; and a sample treatment buffer. In one alternative, the sample treatment buffer is strongly denaturing. Optionally, antibodies in the antibody-microparticle strip are covalently bound to microparticles. Alternatively, the microparticles include an aldehyde group. In one alternative, the sample treatment buffer includes sodium perchlorate as an oxidizing agent. Alternatively, the sample treatment buffer includes 50 mM Imidazole, pH 7.0, 1M LiSCN, 0.5M GuSCN, 1% Brij 35, 500 mM $NaClO_4$. Optionally, the sample treatment buffer includes 50 mM Imidazole, pH 7.0, 1M LiSCN, 0.5M GuSCN, 1% Brij 35 and lithium perchlorate. In another alternative, the sample treatment buffer includes 50 mM Imidazole, pH 7.0, 1M LiSCN, 0.5M GuSCN, 1% Brij 35 and sodium nitrite. Optionally, the sample treatment buffer is 50 mM Imidazole, pH 7.0, 1M LiSCN, 0.5M GuSCN, 1% Brij 35, 2.0925 g/L $K_3Fe(CN)_6$. In one configuration, the sample treatment buffer includes STB057 50 mM Imidazole, pH 7.0, 1.5M NaSCN, 0.5M GuSCN, 1% Brij 35, 2.0925 g/L $K_3Fe(CN)_6$. In another configuration, the sample treatment buffer includes STB058 50 mM Imidazole, pH 7.0, 0.75M LiSCN, 0.75M NaSCN, 0.5M GuSCN, 1% Brij 35, 2.0925 g/L KFeCN. Optionally, the system further includes a second lateral flow test strip, the second lateral flow test strip providing for a percent of HbA1C concentration and providing for the total amount of hemoglobin, an antibody-microparticle stripe on the second lateral flow test strip.

In one embodiment, a method for determining a concentration of hemoglobin A1C includes providing a system including a first lateral flow test strip, the first lateral flow test strip providing for a percent of HbA1C concentration and providing for the total amount of hemoglobin, an antibody-microparticle stripe on the first lateral flow test strip; a conjugate stripe on the first lateral flow test strip; and a sample treatment buffer. The method further includes flowing a sample along the first and second lateral flow test strips. Optionally, the system further includes a sample treatment buffer; and the method further includes mixing the sample with the sample treatment buffer; flowing the sample to the microparticle stripe on the first lateral flow test strip; flowing the sample to the conjugate stripe; and measuring an optical feature of the first lateral flow test strips. In one configuration, the sample treatment buffer is strongly denaturing. Optionally, antibodies in the antibody-microparticle stripe are covalently bound to microparticles. In one alternative, the microparticles include an aldehyde group. In one alternative, the sample treatment buffer includes sodium perchlorate as an oxidizing agent. Alternatively, the sample treatment buffer includes 50 mM Imidazole, pH 7.0, 1M LiSCN, 0.5M GuSCN, 1% Brij 35, 500 mM $NaClO_4$. In another embodiment, the sample treatment buffer includes 50 mM Imidazole, pH 7.0, 1M LiSCN, 0.5M GuSCN, 1% Brij 35, 2.0925 g/L $K_3Fe(CN)_6$. Alternatively, the sample treatment buffer includes STB057 50 mM Imidazole, pH 7.0, 1.5M NaSCN, 0.5M GuSCN, 1% Brij 35, 2.0925 g/L $K_3Fe(CN)_6$. In one configuration, the sample treatment buffer includes STB058 50 mM Imidazole, pH 7.0, 0.75M LiSCN, 0.75M NaSCN, 0.5M GuSCN, 1% Brij 35, 2.0925 g/L KFeCN.

In one embodiment, a system for determining a concentration of hemoglobin A1C includes a first lateral flow test strip, the first lateral flow test strip providing for a percent of HbA1C concentration and providing for the total amount of hemoglobin; an antibody-microparticle stripe on the first lateral flow test strip; a conjugate stripe on the first lateral flow test strip; and a sample treatment buffer, wherein the sample treatment buffer is strongly denaturing, and antibodies in the antibody-microparticle stripe are covalently bound to microparticles. Optionally, the microparticles include an aldehyde group. In one alternative, the sample treatment buffer includes sodium perchlorate as an oxidizing agent. Alternatively, the sample treatment buffer includes 50 mM Imidazole, pH 7.0, 1M LiSCN, 0.5M GuSCN, 1% Brij 35, 500 mM $NaClO_4$. Alternatively, the sample treatment buffer includes STB058 50 mM Imidazole, pH 7.0, 0.75M LiSCN, 0.75M NaSCN, 0.5M GuSCN, 1% Brij 35, 2.0925 g/L KFeCN. Optionally, the antibody is monoclonal.

BRIEF DESCRIPTION OF THE DRAWINGS

FIGS. 14A and 14B show graphs of variant bias for testing performed with three particular buffers STB, STB033, and STB065 for the HbC variant;

DETAILED DESCRIPTION

Figure 1A:
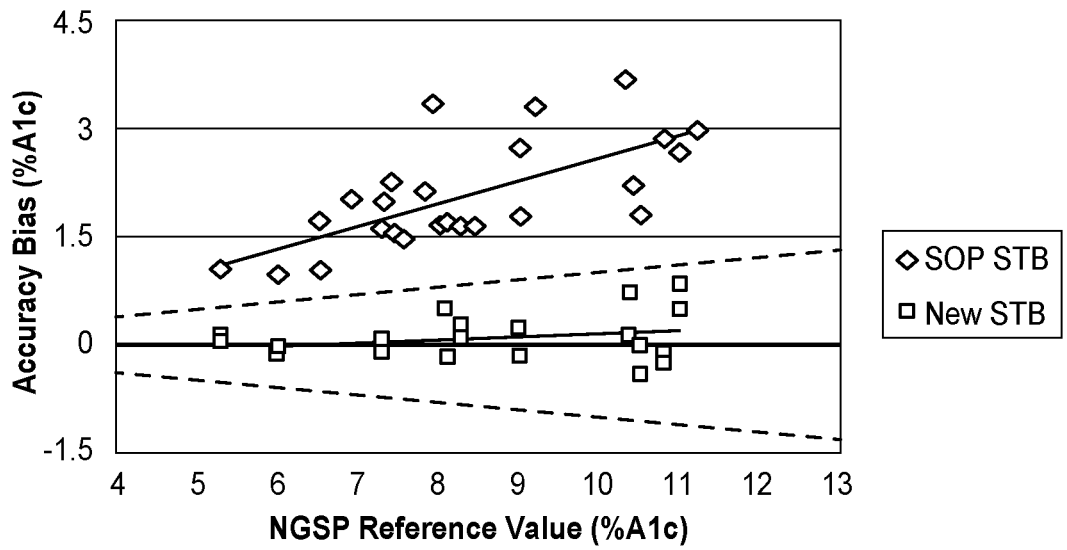
FIGS. 1A and 1B show graphs of the correlation and bias percentage for a traditional sample treatment buffer and one embodiment of a new sample treatment buffer.

Certain terminology is used herein for convenience only and is not to be taken as a limitation on the embodiments of the systems and methods for interference correction from hemoglobin variants. In the drawings, the same reference letters are employed for designating the same elements throughout the several figures. In many embodiments, a sample treatment buffer that is strongly denaturing is used in combination with a microparticle that is strongly bound to an antibody. In many embodiments, this may be a covalent bond. Additionally, in many configurations, a sample treatment buffer is used that includes stability at room temperature. In many configurations, this is accomplished by configuring the oxidizing agent. This oxidizing agent may be sodium perchlorate.

Polymer Technology Systems, Inc. (PTS), manufactures the A1CNow®, a Point-of-Care device for measuring HbA1C. This test is an immunochemistry (antigen-antibody)-based system which performs well unless the patient has hemoglobin variances (HbS and HbC are the two most common variants) which create false high results as much as 30%. In many places herein, A1C bias is referenced. A1C bias relates to the absolute A1C basis in relation to the percentage of A1C as a unit. For example, a 6% A1C sample with 2% A1C bias Tosoh reference result is 6% A1C, and the A1CNow® result is 8% A1C. In the art, the Tosoh G8 HPLC Analyzer (merely referred to as "Tosoh" herein) utilizes the Gold Standard Ion-Exchange method of HbA1C measurement and, therefore, many times is used as a reference. Other highly regarded testing methods/systems for HbA1C, especially those including hemoglobin variants, include the Trinity (Primus) HPLC (affinity), which has been used as the reference value assignment method for our HbS and HbC samples. At multiple points herein, the bias of the system or test is referred to. Generally, bias refers to the relative % bias (percent bias). For example, for a sample with a Tosoh value of 6% A1C and the A1CNow® value is 8% A1C, the bias percentage would be: % Bias=33% (A1C bias=2% A1C).

The occurrence of variants may greatly affect the use and reliability of A1C testing. For instance, Hb variants affect approximately 10% of African-Americans (10% African-Americans carry either HbS or HbC) and 2% Hispanic Americans. In the United States, HbS is the most common variant, HbC is the second most common variant, and HbE is the third most common variant. NGSP has put a lot of emphasis recently on the requirement to eliminate the interference of Hb variants. The current acceptance limit for Hb variants is <±7% relative bias (it was ±10% in 2012 and before). The FDA has requested that Hb variant interference for diagnosis/screening indication be eliminated.

There are at least five methodologies for solving the issues that variants pose to the accuracy of Hb testing. Typical systems used for Hb detection include the A1CNow+® and the A1CNow® systems, and those described in US Patent Application Publication No. 20050227370. A first approach calls for a stronger sample treatment buffer (STB) while using the current microparticles and current Ab (antibody). Currently, a polyclonal antibody is used. As is known, polyclonal antibodies typically have lower specificity than monoclonal antibodies. The result of using a stronger STB, as show in Table 1, is that for two of the variants, the bias is significantly reduced. One issue that arises, however, is that a strong STB tends to reduce the signal. It is theorized that this is due to the antibody detaching from the microparticles. Typically, a competitive assay or sandwich assay is used in the determination of Hb; however, other assay techniques may be used in alternatives.

TABLE 1

| # | Description | Result | Comment |
|---|---|---|---|
| Approach I | New STB Only Stronger sample treatment buffer Current MP (Passive Ab absorption) Current AB | For HbC: Be able to correct HbC interference problem (reduced the relative % bias to <4%) For HbS: Significantly reduced % bias from 30% bias to ~7-8% (but not completely solve HbS problem). | If STB too stronger, signal is too light (lost assay curve), may due to Ab detaching from MP Need stronger Ab coupling to handle different stronger STB |

TABLE 1-continued

| # | Description | Result | Comment |
|---|---|---|---|
| Approach II | New mAbs Only<br>New monoclonal antibody<br>No STB change (current sample treatment buffer<br>Current MP (Passive Ab absorption) | For HbC: Be able to correct HbC interference problem (reduced the relative % bias to <4%)<br>For HbS: Significantly reduced %bias from 30% to ~8% (but not completely solve HbS problem) | Only reduced to ~7-8% bias and haven't been able reduce % bias further |
| Approach III | New STB + New MP + Current Ab<br>Stronger Ab-MP coupling (New ALD MP for Covalent coupling)<br>Different stronger sample treatment buffer<br>No Ab change (current Ab) | Be able to correct bias caused by both HbS and HbC interferences (relative % bias for both HbS and HbC to <3%) | With stronger Ab-MP coupling (covalent coupling to ALD latex) to prevent Ab detach, different stronger STB can be used in the system to correct interference |
| Approach IV | New mAb + New STB<br>New mAb<br>Current MP (passive Ab coupling)<br>New STB (stronger STB) | No assay curve (Signal was too light) | Need stronger Ab-MP coupling (covalent binding) to prevent Ab detach |
| Approach V | New mAb + New STB + New MP<br>New mAb<br>New STB (stronger STB)<br>New MP (covalent Ab coupling) | No assay curve (had signal, but cannot inhibit the signal in the system we are currently using) | Not compatible with the system used in approach III<br>Need more assay optimization |

A second approach includes using an antibody with a higher specificity. This involves switching to a monoclonal antibody. This approach also yielded some results, reducing the basis for both HbC and HbS somewhat. However, the reduction in bias appeared to be capped at approximately 7% to 8% for HbS.

A third alternative involves the usage of stronger microparticle-antibody bonding. Additionally, in most configurations, the usage of a stronger sample treatment buffer is used as well. This alternative is shown in alternative three of the chart of Table 1. Although in the previous alternative/approach 1 the usage of a stronger STB resulted in improved results, it is thought that the stronger STB resulted in the dissociation of the antibody with the microparticle. In order to reduce the occurrence of this dissociation, a stronger bond may be created between the antibody and the microparticle. In some embodiments, this strong bond is a covalent bond. In some alternatives, the beads are bound to antibodies using an aldehyde bond. The double bonded oxygen that is part of the aldehyde group is a proton acceptor, thereby making it conducive to forming a covalent bond with a proton donor. By binding an aldehyde group to the microparticle, a covalent bond may be formed between the antibody and the microparticle having an aldehyde group. In some alternatives, a ketone group might be used; however the covalent bonding properties will likely be reduced; therefore, the STB strength may correspondingly be reduced. In many embodiments, the microparticle is composed of latex, and the latex includes an aldehyde group.

A fourth approach includes the usage of a monoclonal antibody and a stronger STB. Standard coupling between the microparticle and the antibody is used. This approach resulted in a signal that was too low (too light). This approach appears to need stronger antibody-microparticle binding. This is thought to be because the combination of the stronger STB and the monoclonal antibody lead to too strong of a preference for dissociation between the antibody and the microparticle.

A fifth approach is thought to be optimal and generates improved results. The fifth approach replaces the traditional polyclonal antibody with a monoclonal antibody, utilizes a stronger STB, and utilizes a stronger bond between the antibody and the microparticle. In many embodiments, this may be an aldehyde bond. Based on the formulations used experimentally, it is believed that a somewhat weaker STB might be used in some embodiments. Alternatively, a bond of a different strength between the antibody and microparticle may be formed. It is believed that this system may be promising; however, adjustments to the assay must be made before it becomes viable.

The following describe some possible STBs. An exemplary STB that has stronger denaturing and cytotropic characteristics as compared to the standard buffer has been used previously. The standard STB used is 5 mM Imidazole, 2% Zwittergent, 2.0925 g/L KFeCN, 112 mM NaCl, 0.1% Surfynol, pH 7.5. An exemplary and stronger STB is 20 mM Glycine, 1M LiSCN, 1% Triton, 2.0925 g/L KFeCN, 0.5M GuSCN, pH 9. The use of the stronger STB alone reduces the HbC variant issues to acceptable levels; however, it does not have enough impact to reduce HbS variant issues to acceptable levels. Additionally, numerous oxidant replacements for the buffers provided are possible. In the STBs, typically an oxidant of $K_3Fe(CN)_6$ is used. Alternatively, sodium perchlorate, lithium perchlorate, or sodium nitrite may be used as well as other oxidants that may provide for the formation of methemoglobin.

FIGS. 1A through 2B show graphs of the correlation and bias percentage, as well as a Table 2 comparing the old STB (5 mM Imidazole, pH 7.5, 0.1125M NaCl, 2% Zwittergent-3,14, 0.1% Surfynol-485, 2.0925 g/L $K_3Fe(CN)_6$) as compared to the new STB058.

TABLE 2

| Hb Variant | Current SOP STB | | New STB | | |
|---|---|---|---|---|---|
| | Avg Bias (% A1C) | % Bias | Avg Bias (% A1C) | % Bias | % Correction |
| HbC | 2.06 | 24.5% | 0.09 | 0.9% | 95.6% |
| HbS | 2.30 | 28.4% | 0.52 | 7.3% | 77.2% |

Figure 2A:
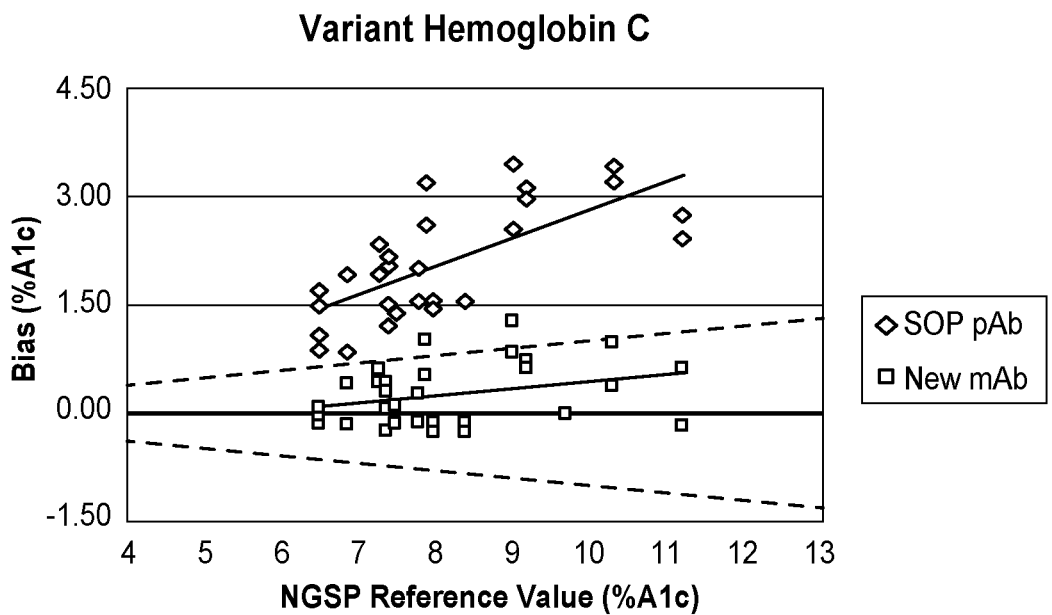
FIGS. 2A and 2B show graphs of the correlation and bias percentage, as well as a table comparing a polyclonal antibody compared to the new monoclonal antibody.
Figure 2B:
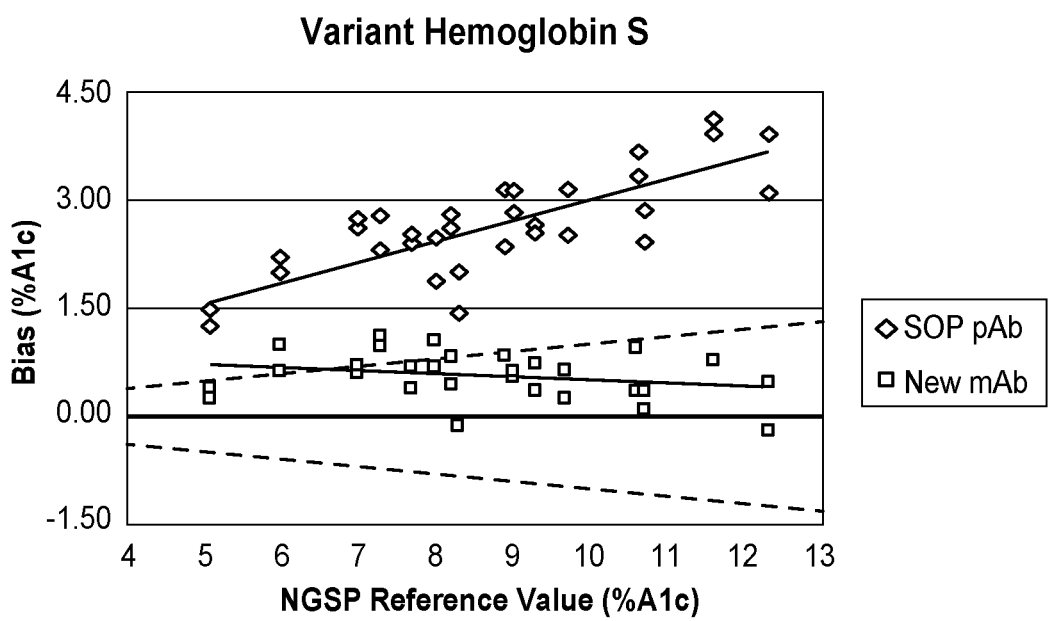

FIGS. 2A-2B show graphs of the correlation and bias percentage, as well as a Table 3 comparing the old polyclonal antibody compared to the new monoclonal antibody. The bias was reduced for both HbC and HbS; however, the HbS was still not within desired levels.

TABLE 3

| Sample | Current SOP pAb | | New mAb-2403 | | |
|---|---|---|---|---|---|
| | Avg Bias (% A1C) | % Bias | Avg Bias (% A1C) | % Bias | % Correction |
| HbA | 0.01 | 0.1% | 0.01 | 0.2% | — |
| HbC | 2.00 | 24.2% | 0.31 | 3.6% | 84.3% |
| HbS | 2.79 | 32.0% | 0.69 | 8.3% | 75.4% |

Various STBs are possible for use as a strong STB. A strong STB was needed to function with the stronger Ab-MP coupling. A variety of STB and microparticle combinations were tested, as shown in Table 4 below. Additional STBs using different oxidizing agents are shown later in this disclosure.

TABLE 4

| | | Condition 1 | Condition 2 | Condition 3 | Condition 4 | Condition 5 |
|---|---|---|---|---|---|---|
| | Buffer | Current | Current | STB033 | STB057 | STB058 |
| | Microparticle | Current | New | New | New | New |
| HbS | Avg Bias (% A1C) | 2.68 | 2.78 | 0.52 | 0.40 | 0.20 |
| | % Bias | 31.3% | 33.2% | 6.5% | 4.4% | 2.7% |
| HbC | Avg Bias (% A1C) | 2.22 | 2.41 | 0.09 | 0.04 | 0.05 |
| | % Bias | 26.3% | 29.1% | 0.9% | 0.5% | 0.2% |

Using a new Aldehyde MP to have stronger Ab-MP coupling is such that the system can tolerate a much stronger buffer for sample treatment (without Ab detachment). The use of different stronger buffers to denature and present the antigen better for interference reduction was achieved by the combination shown.

The buffers tested are as follows:
Previous SOP: 5 mM Imidazole, pH 7.5, 0.1125M NaCl, 2% Zwittergent-3,14, 0.1% Surfynol-485, 2.0925 g/L $K_3Fe(CN)_6$
STB033: 50 mM Imidazole, pH 7.0, 1M LiSCN, 0.5M GuSCN, 1% Brij 35, 2.0925 g/L $K_3Fe(CN)_6$
STB057: 50 mM Imidazole, pH 7.0, 1.5M NaSCN, 0.5M GuSCN, 1% Brij 35, 2.0925 g/L $K_3Fe(CN)_6$
STB058: 50 mM Imidazole, pH 7.0, 0.75M LiSCN, 0.75M NaSCN, 0.5M GuSCN, 1% Brij 35, 2.0925 g/L $K_3Fe(CN)_6$
STB065: 50 mM Imidazole, pH 7.0, 1M LiSCN, 0.5M GuSCN, 1% Brij 35, 500 mM $NaClO_4$ and various different concentrations of sodium perchlorate
STB099: 50 mM Imidazole, pH 7.0, 1M LiSCN, 0.5M GuSCN, 1% Brij 35 plus various concentrations of lithium perchlorate
STB098: 50 mM Imidazole, pH 7.0, 1M LiSCN, 0.5M GuSCN, 1% Brij 35 plus various concentrations of sodium nitrite Before the introduction of the embodiments of a combination of stronger STB and Ab-MP coupling, the system had about 30% positive bias when testing with Hb variant samples.

The new system can significantly reduce the bias caused by Hb variants.

Figure 1B:
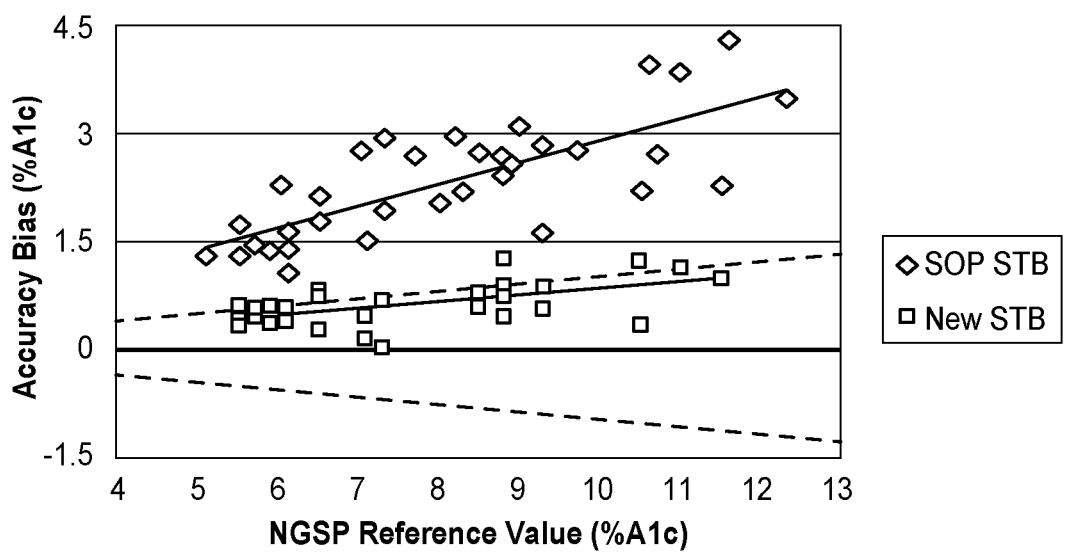

STB058 gave good results. FIGS. 1A-1B show graphs of the correlation and bias percentage, as well as a table (Table 1) comparing the old STB (5 mM Imidazole, pH 7.5, 0.1125M NaCl, 2% Zwittergent-3,14, 0.1% Surfynol-485, 2.0925 g/L $K_3Fe(CN)_6$) as compared to the new STB058.

Figure 3A:
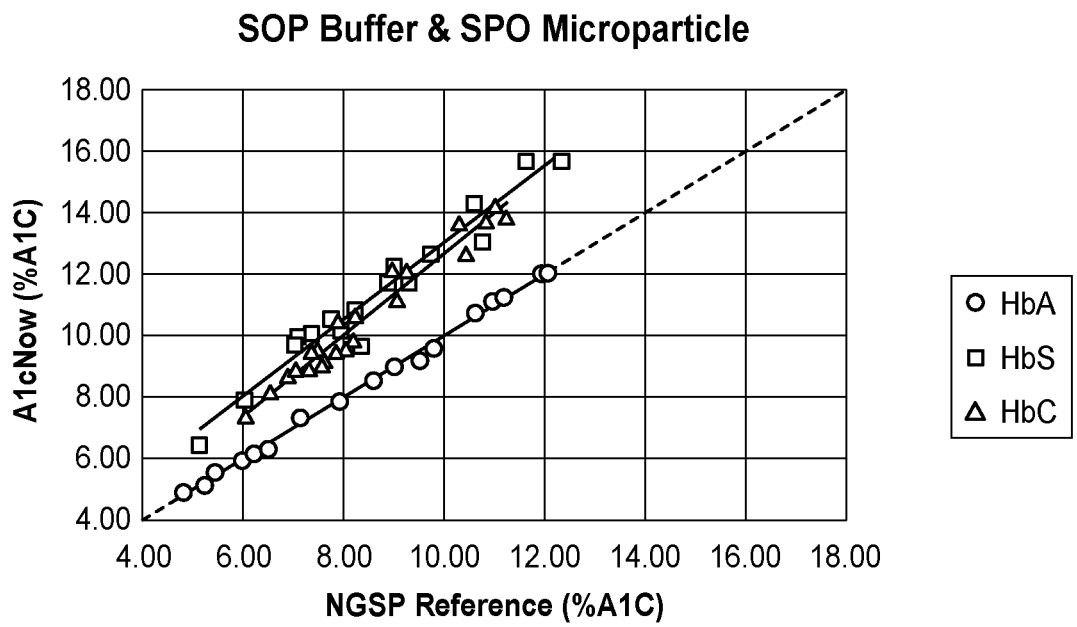
FIG. 3A shows a correlation graph.
Figure 3B:
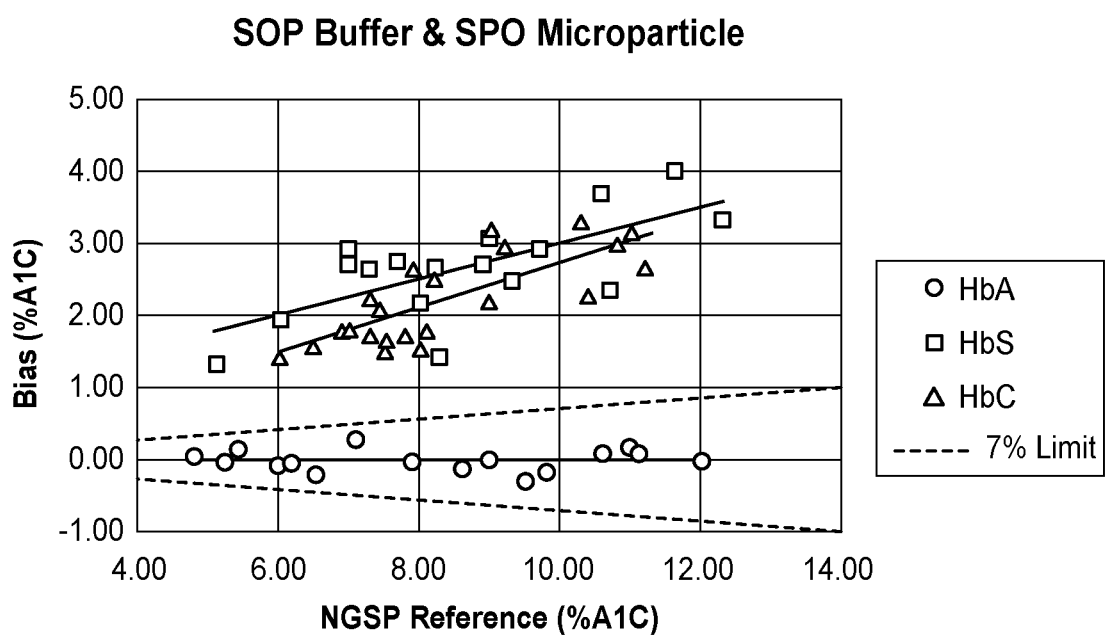
FIG. 3B shows a bias graph for a prior art system.

FIG. 3A shows a correlation graph, and FIG. 3B shows a bias graph for the currently used system. The SOP STB buffer is 5 mM Imidazole, pH 7.5, 0.1125M NaCl, 2% Zwittergent-3,14, 0.1% Surfynol-485, 2.0925 g/L $K_3Fe(CN)_6$. MP-Ab coupling is accomplished via passive antibody absorption. As shown, there is a high positive bias caused by HbS and HbC variant interferences.

Figure 4A:
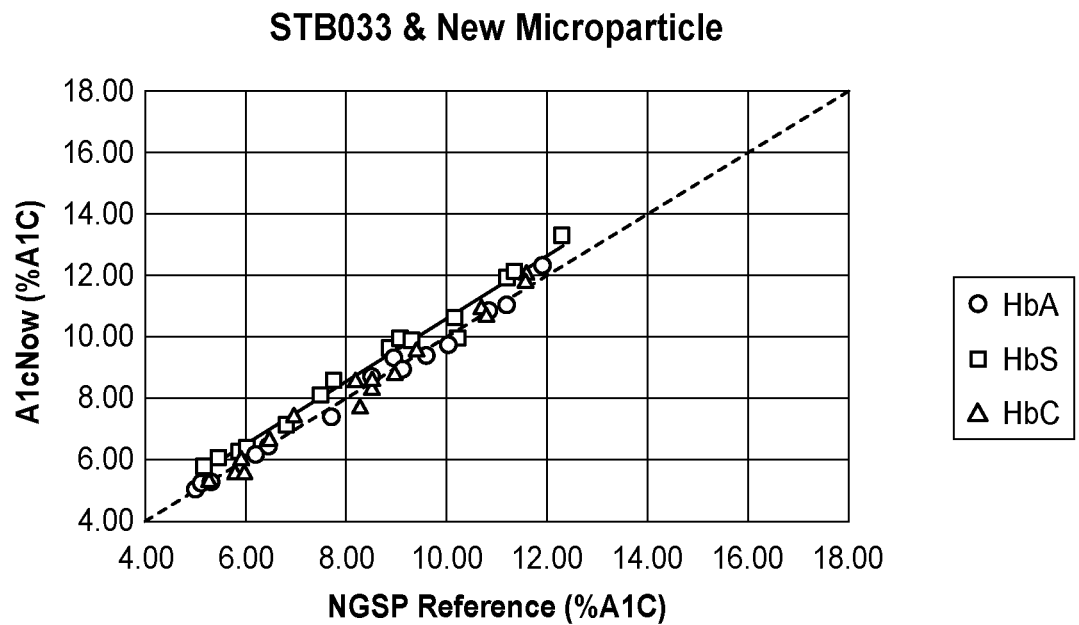
FIGS. 4A and 4B show a correlation graph and a bias graph, respectively, for one embodiment of the stronger STB033 buffer and the ALD MP.
Figure 4B:
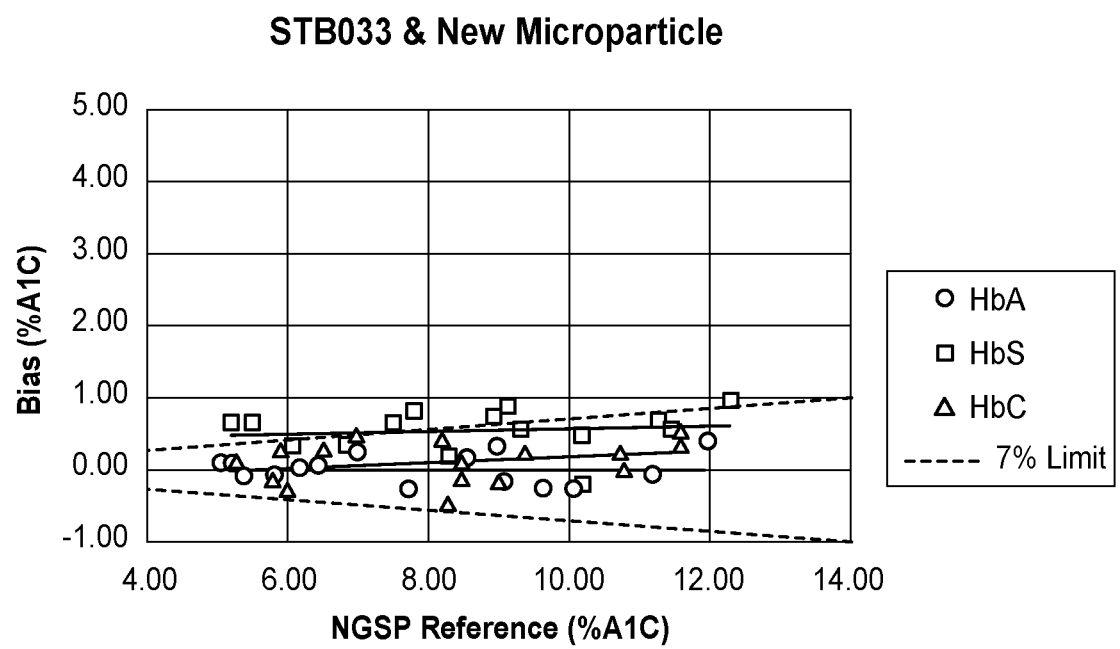

FIGS. 4A and 4B show a correlation graph and a bias graph, respectively, for the stronger STB033 buffer and the ALD MP. As shown by the data for the new buffer STB033 with ALD MP and current Ab (stronger Ab-MP coupling and stronger sample treatment buffer), the bias is significantly reduced. Although in this embodiment the STB buffer (STB033) is 50 mM Imidazole, pH 7.0, 1M LiSCN, 0.5M GuSCN, 1% Brij 35, 2.0925 g/L $K_3Fe(CN)_6$, various buffers with similar properties are possible. As described above, in the embodiment shown, MP-Ab coupling includes the use of an ALD MP with stronger Ab coupling. This results in significantly reduced bias caused by HbS interference (bias ~6.5%) and bias caused by HbC variant (~1%).

Figure 5A:
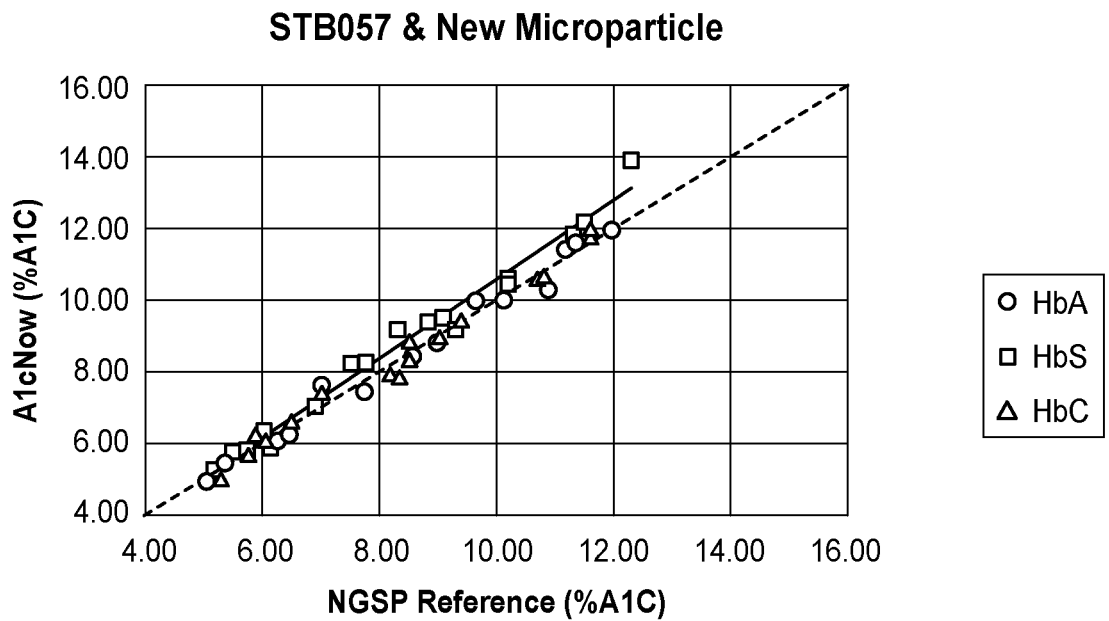
FIGS. 5A and 5B show correlation data and bias data, respectively, for one embodiment of a sample treatment buffer with one embodiment of an ALD MP.
Figure 5B:
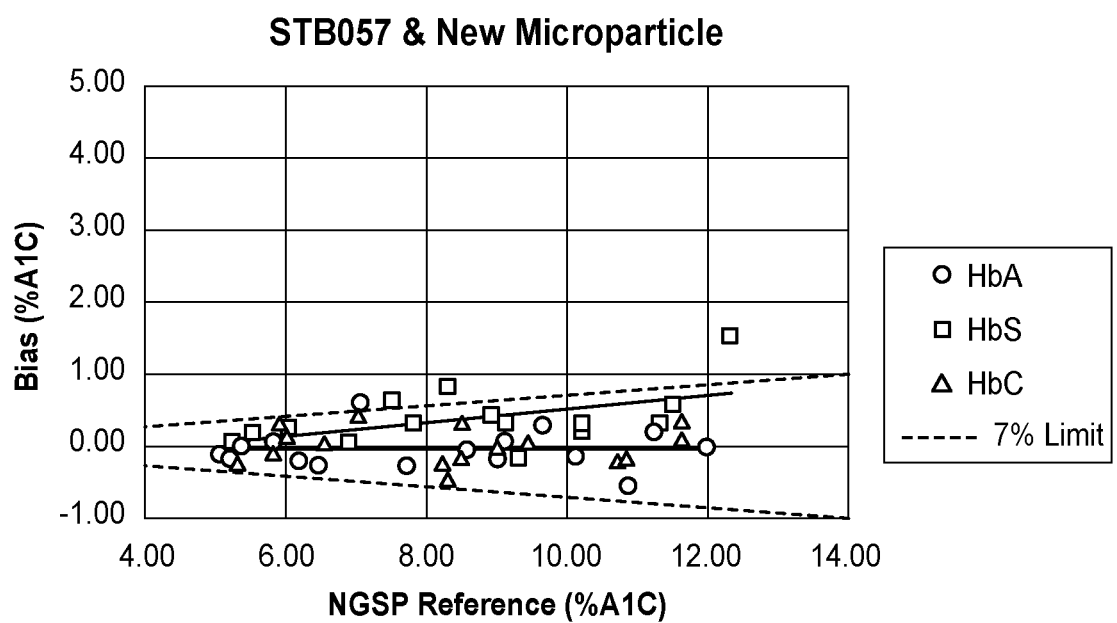

FIGS. 5A and 5B show correlation data and bias data, respectively, for the new buffer STB057 with ALD MP and current Ab. This system shows stronger Ab-MP coupling and a stronger sample treatment buffer. The STB buffer (STB057) is 50 mM Imidazole, pH 7.0, 1.5M NaSCN, 0.5M GuSCN, 1% Brij 35, 2.0925 g/L $K_3Fe(CN)_6$. The MP-Ab coupling is ALD MP with stronger Ab coupling. The result is significantly reduced bias caused by HbS interference (bias ~4.4%) and bias caused by HbC variant (<1%).

Figure 6A:
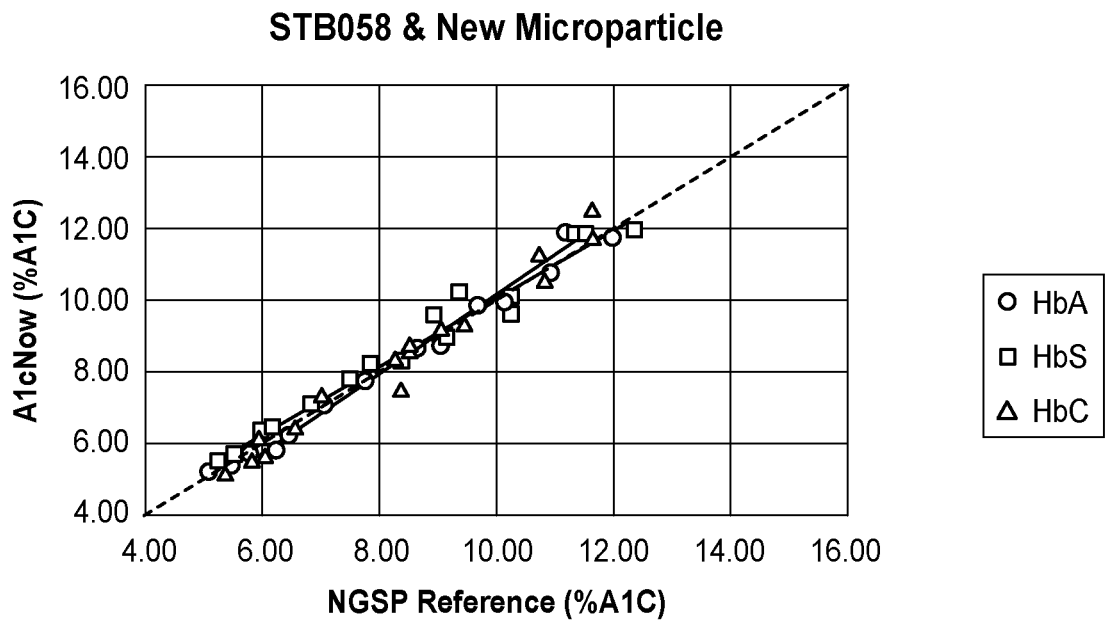
FIGS. 6A and 6B show correlation data and bias data, respectively, for new buffer STB058 with ALD MP and current Ab.
Figure 6B:
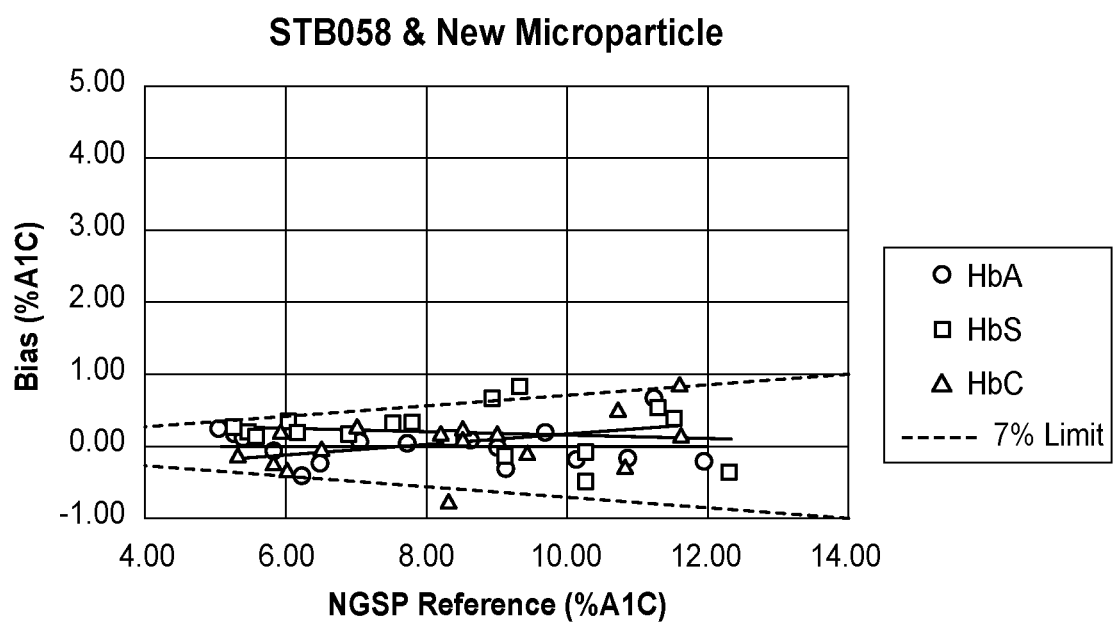

FIGS. 6A and 6B show correlation data and bias data, respectively, for the new buffer STB058 with ALD MP and current Ab. This system shows stronger Ab-MP coupling and a stronger sample treatment buffer. The STB buffer (STB058) is 50 mM Imidazole, pH 7.0, 0.75M LiSCN, 0.75M NaSCN, 0.5M GuSCN, 1% Brij 35, 2.0925 g/L KFeCN. The MP-Ab coupling is ALD MP with stronger Ab coupling. The result is significantly reduced bias caused by HbS interference (bias ~2.7%) and bias caused by HbC variant (<1%).

Figure 7A:
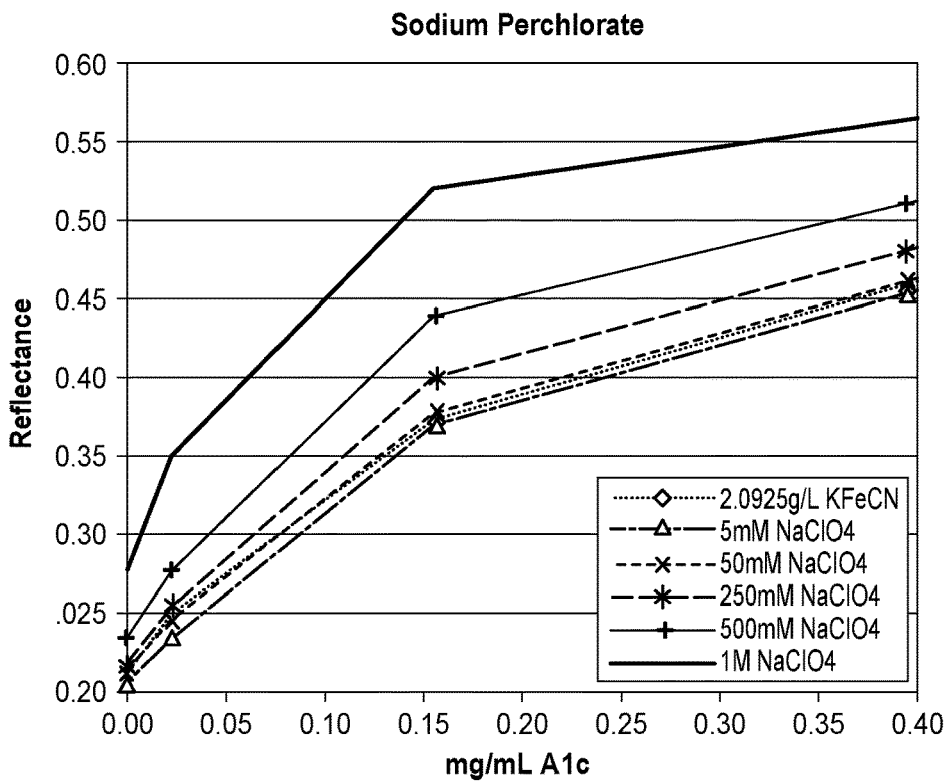
FIGS. 7A and 7B show graphs of results from testing conducted with an STB plus the noted concentrations of sodium perchlorate and lithium perchlorate respectively.
Figure 7B:
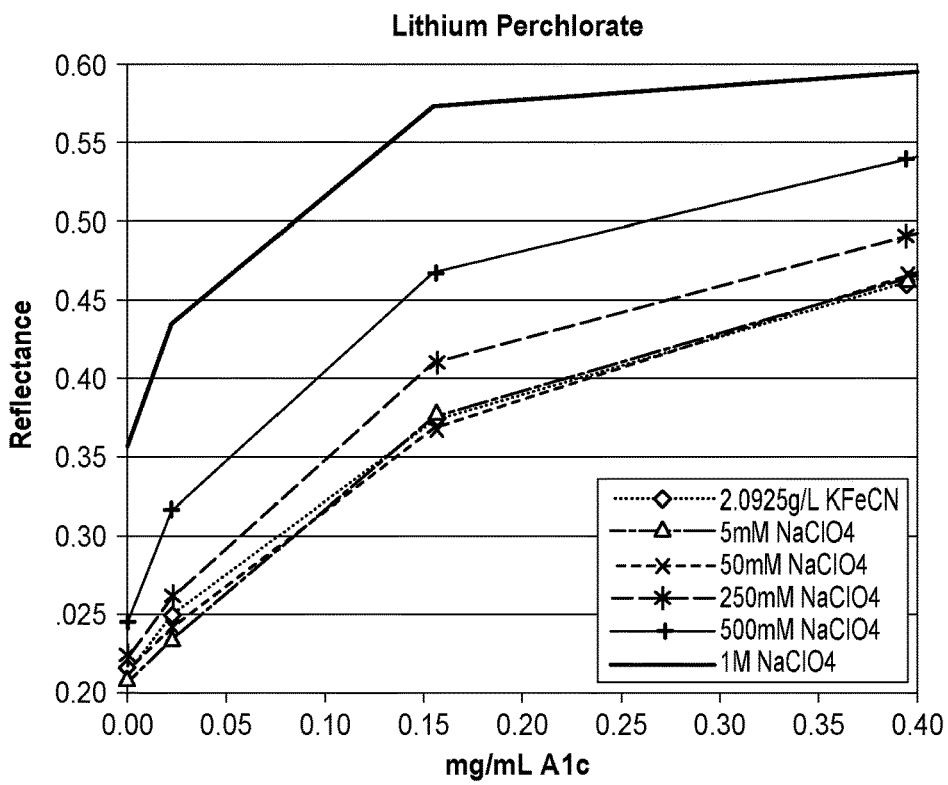

In various embodiments, the formulation may include a replacement oxidizing agent that replaces the $K_3Fe(CN)_6$. Sodium perchlorate, lithium perchlorate, or sodium nitrite may be used as well as other oxidants that may provide for the formation of methemoglobin. FIGS. 7A and 7B, show testing conducted with an STB of 50 mM Imidazole, pH 7.0, 1M LiSCN, 0.5M GuSCN, 1% Brij 35 plus the noted concentrations of sodium perchlorate and lithium perchlorate respectively. As shown, these oxidizing agents are a similar substitute for $K_3Fe(CN)_6$. In both instances, a concentration of 5000 mM seems optimal.

Table 5 below summarizes the results of testing these oxidizing agent substitutes. Some of the concentrations of the oxidizing agents that do not meet specifications are 500 mM $LiClO_4$, 1M $NaClO_4$, and 1M $LiClO_4$. Note the delta R and the underlined values that indicate the results may not meet useful specifications.

TABLE 5

| Oxidant | Bovine | Low | Mid | High | Delta R | Delta (H − M) |
|---|---|---|---|---|---|---|
| 2.0925 g/L KFeCN | 0.2149 | 0.2485 | 0.3733 | 0.4604 | 0.2119 | 0.0871 |
| 5 mM NaClO$_4$ | 0.2043 | 0.2354 | 0.3706 | 0.4573 | 0.2219 | 0.0867 |
| 50 mM NaClO$_4$ | 0.2098 | 0.2457 | 0.3765 | 0.4607 | 0.2150 | 0.0842 |
| 250 mM NaClO$_4$ | 0.2174 | 0.2525 | 0.4015 | 0.4813 | 0.2288 | 0.0799 |
| 500 mM NaClO$_4$ | 0.2330 | 0.2790 | 0.4390 | 0.5100 | 0.2310 | 0.0709 |
| 1M NaClO$_4$ | 0.2799 | <u>0.3504</u> | 0.5217 | 0.5643 | 0.2138 | 0.0425 |
| 5 mM LiClO$_4$ | 0.2102 | 0.2354 | 0.3749 | 0.4636 | 0.2282 | 0.0887 |
| 50 mM LiClO$_4$ | 0.2117 | 0.2405 | 0.3690 | 0.4647 | 0.2242 | 0.0957 |
| 250 mM LiClO$_4$ | 0.2207 | 0.2606 | 0.4100 | 0.4899 | 0.2293 | 0.0799 |
| 500 mM LiClO$_4$ | 0.2449 | <u>0.3142</u> | 0.4694 | 0.5391 | 0.2249 | 0.0696 |
| 1M LiClO$_4$ | 0.3535 | <u>0.4342</u> | 0.5725 | 0.5933 | <u>0.1591</u> | 0.0208 |

Figure 8A:
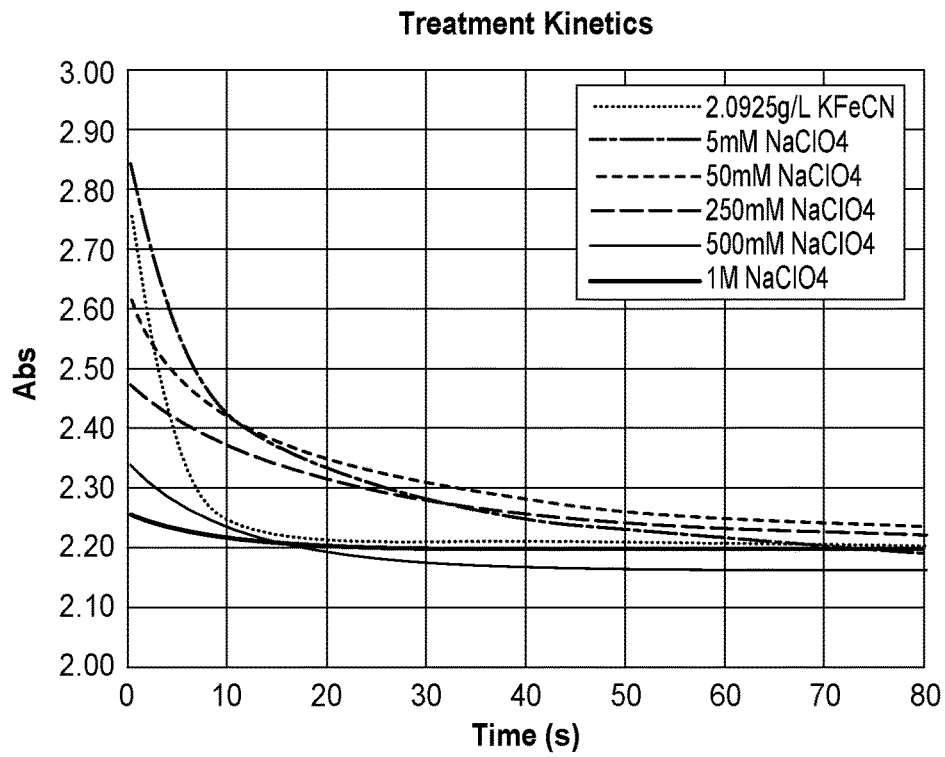
FIGS. 8A and 8B show graphs of results of the oxidizing agent sodium perchlorate tested for sample treatment kinetics and red blood cell lysis kinetics.
Figure 8B:
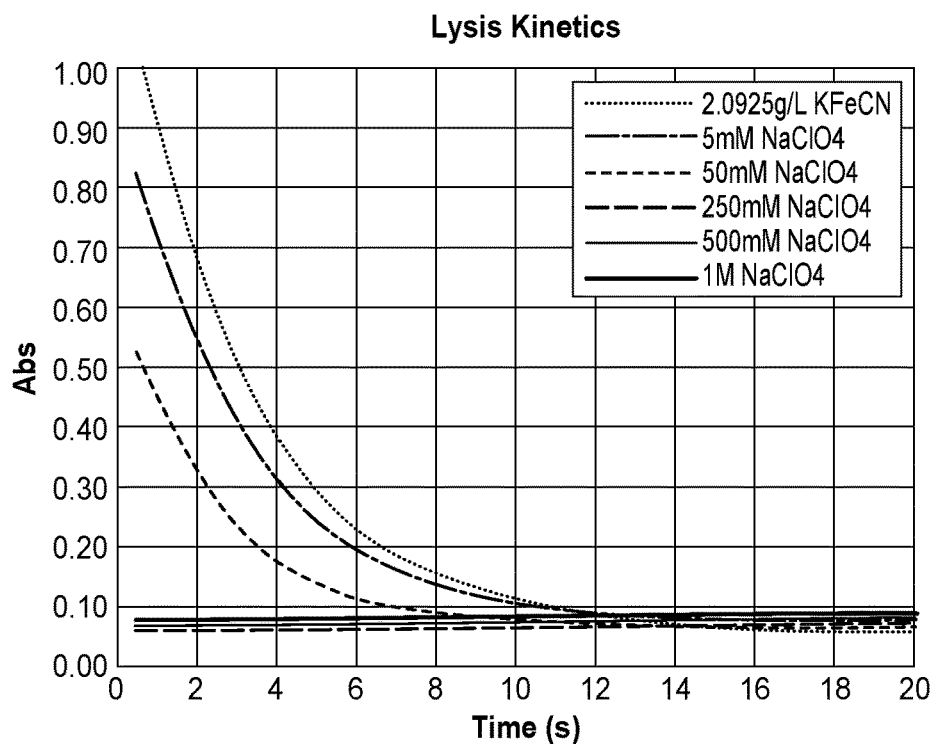

Additionally, the oxidizing agent sodium perchlorate was tested for sample treatment kinetics and red blood cell lysis kinetics. The results are shown in Table 6 below and FIGS. 8A and 8B. The idea of this is that, with certain concentrations of the oxidizing agent, the treatment of the sample must take place sufficiently quickly and the RBCs must be lysised sufficiently quickly to maintain a user friendly pre-mixing scheme as is performed with PTS's redwood sampler that is standard in A1C tests. Treatment timing is slow for 5, 50, and 250 mM NaClO$_4$ at greater than 60 sec. Lysis timing is good for all conditions with less than 14 sec. The only condition that is operable for the timing and usage of the redwood sampler is 500 mM NaClO$_4$. Therefore, sodium perchlorate may be used, at 500 mM NaClO$_4$, as an alternate oxidant. Note that the underlined values denote Δ (L-H) that may not comport with specifications.

TABLE 6

| Oxidant | Bovine | Low | Mid | High | Δ (L − H) | Δ (B − H) |
|---|---|---|---|---|---|---|
| 2.0925 g/L KFeCN | 0.6140 | 0.7555 | 0.7343 | 0.6242 | 0.1313 | −0.0103 |
| 5 mM NaClO$_4$ | 0.6261 | 0.7593 | 0.7368 | 0.6283 | <u>0.1311</u> | −0.0021 |
| 50 mM NaClO$_4$ | 0.6284 | 0.7610 | 0.7321 | 0.6220 | 0.1390 | 0.0064 |
| 250 mM NaClO$_4$ | 0.6221 | 0.7556 | 0.7327 | 0.6206 | 0.1350 | 0.0015 |
| 500 mM NaClO$_4$ | 0.6142 | 0.7414 | 0.7344 | 0.6246 | <u>0.1168</u> | −0.0104 |
| 1M NaClO$_4$ | 0.6070 | 0.7417 | 0.7277 | 0.6211 | <u>0.1206</u> | −0.0142 |
| 5 mM LiClO$_4$ | 0.6259 | 0.7635 | 0.7384 | 0.6288 | 0.1346 | −0.0030 |
| 50 mM LiClO$_4$ | 0.6256 | 0.7588 | 0.7365 | 0.6312 | <u>0.1276</u> | −0.0056 |
| 250 mM LiClO$_4$ | 0.6200 | 0.7527 | 0.7329 | 0.6277 | <u>0.1250</u> | −0.0077 |
| 500 mM LiClO$_4$ | 0.6168 | 0.7489 | 0.7310 | 0.6258 | <u>0.1231</u> | −0.0091 |
| 1M LiClO$_4$ | 0.6182 | 0.7509 | 0.7333 | 0.6290 | <u>0.1219</u> | −0.0108 |

Figure 9:
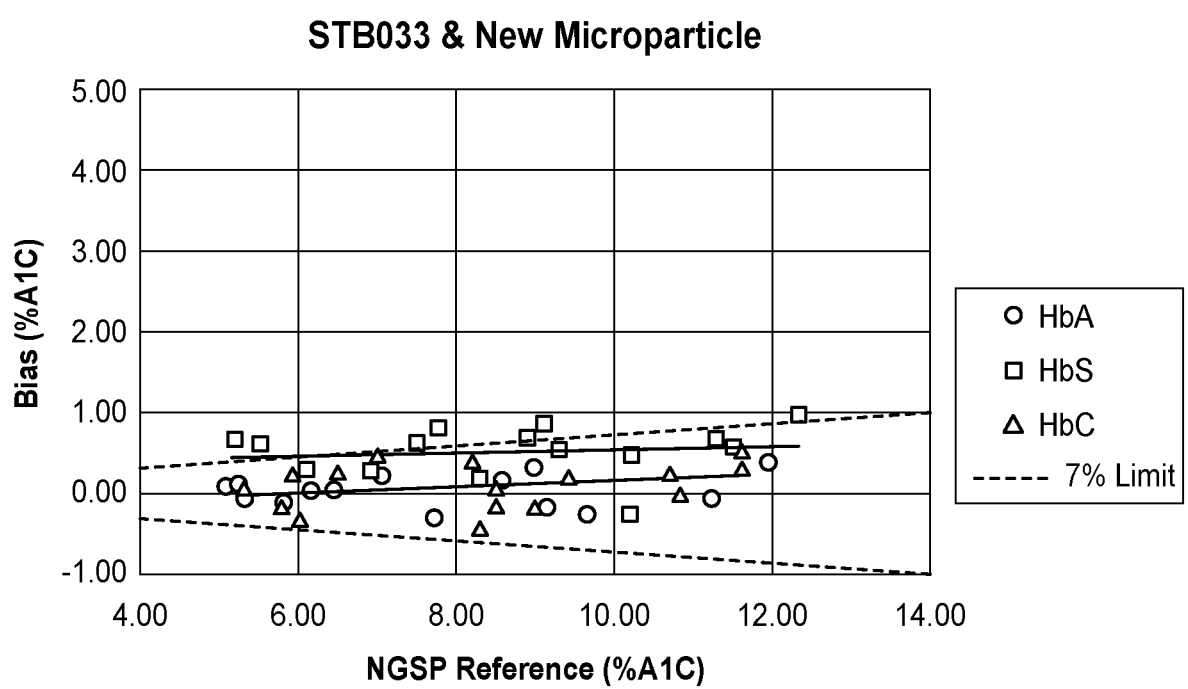
FIGS. 9 and 10 show stability tables and graphs for a mixture including a specific sample buffer solution.

FIG. 9 shows a graph of bias using the STB033 formulation. As is clear from the graph, the usage of this formulation provides for bias within the allowable limit for Hb variants. However, the issue with this formulation is that it degrades over time and, if not placed in cold storage, the variant bias is not within the allowable limits. The same holds true for STB058. See Tables 7 and 8 below. Note that in Tables 7 and 8 the underlined values may provide for results that provide a product that is not useful in commercial applications.

TABLE 7

| | New STB | Buffer Storage | % Relative Bias |
|---|---|---|---|
| HbS Bias | STB033 | Freshly Prepared | 6.4% |
| | STB033 | 3 weeks @ 4° C. | 7.2% |
| | STB033 | 3 weeks @ RT | 7.6% |
| HbC Bias | STB033 | Freshly Made | 1.9% |
| | STB033 | 3 weeks @ 4° C. | 3.1% |
| | STB033 | 3 weeks @ RT | 3.9% |

TABLE 8

| | New STB | Buffer Storage | % Relative Bias |
|---|---|---|---|
| HbS Bias | STB058 | Freshly Prepared | 6.5% |
| | STB058 | 3 weeks @ 4° C. | 5.9% |
| | STB058 | 3 weeks @ RT | 8.7% |
| HbC Bias | STB058 | Freshly Made | 1.1% |
| | STB058 | 3 weeks @ 4° C. | 1.3% |
| | STB058 | 3 weeks @ RT | 3.3% |

Figure 10:
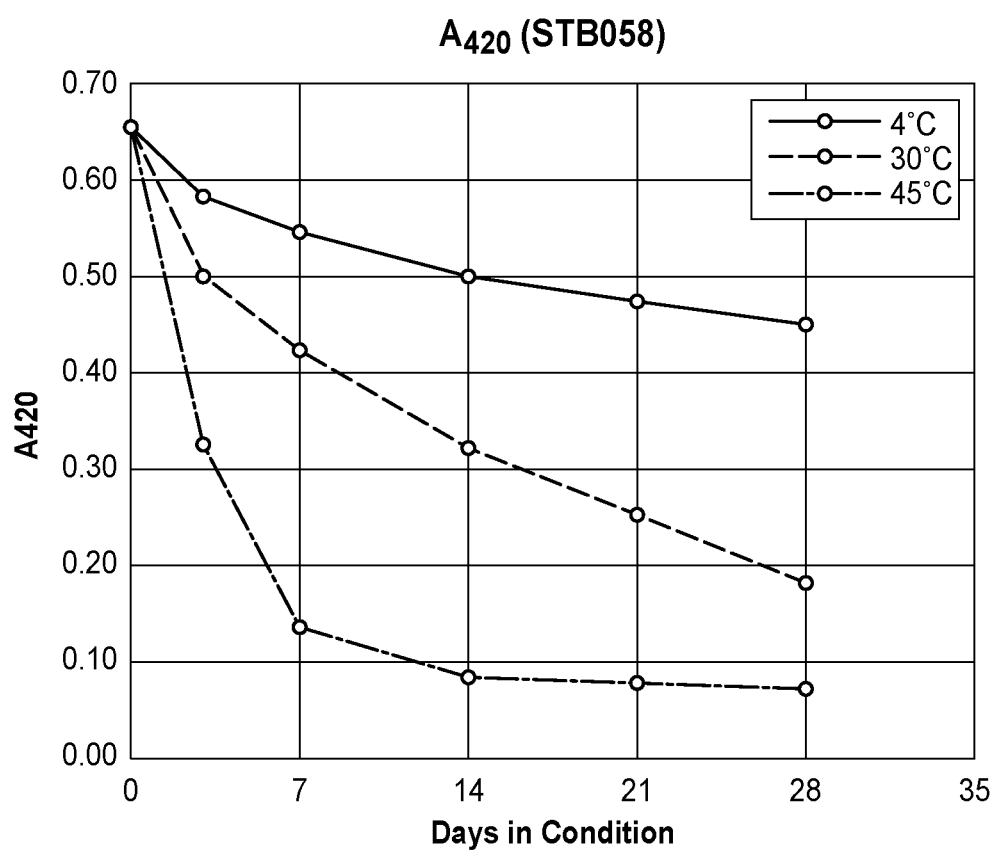
Figure 11:
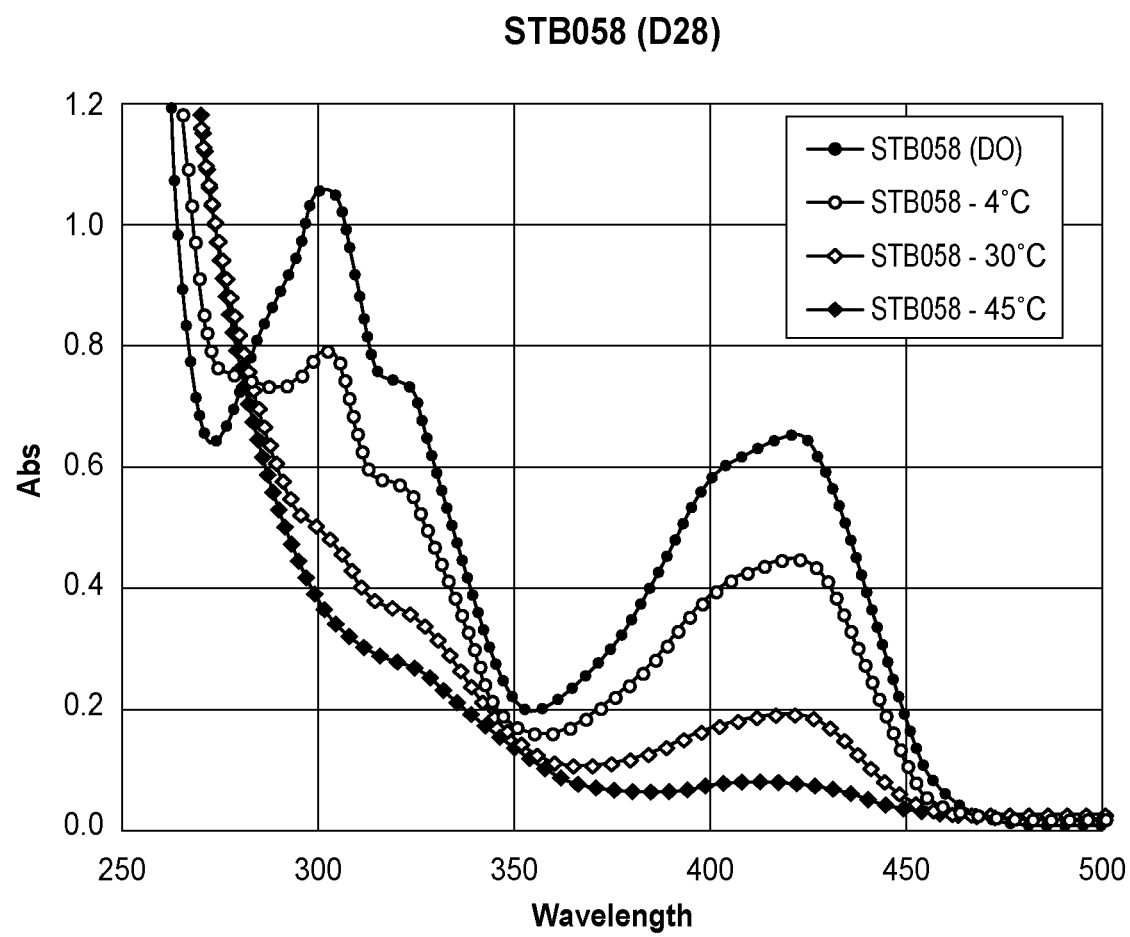
FIG. 11 shows a graph of the absorption wavelength for one of the buffers at various wavelengths.

Table 9 and FIG. 10 show stability tables and graphs for a mixture including STB058. FIG. 11 shows a graph of the absorption wavelength for one of the buffers at various wavelengths. This shows the suitability for this buffer for usage as described herein.

TABLE 9

| | A420 | | | | | | | | |
|---|---|---|---|---|---|---|---|---|---|
| | STB058 | | | % from Day 0 | | | Conc. Of KFeCN (g/L) | | |
| Day | 4° C. | 30° C. | 45° C. | 4° C. | 30° C. | 45° C. | 4° C. | 30° C. | 45° C. |
| 0 | 0.655 | 0.655 | 0.655 | 100% | 100% | 100% | 2.09 | 2.09 | 2.09 |
| 3 | 0.586 | 0.494 | 0.326 | 89% | 75% | 50% | 1.87 | 1.57 | 1.03 |
| 7 | 0.550 | 0.424 | 0.136 | 84% | 65% | 21% | 1.75 | 1.35 | 0.42 |
| 14 | 0.499 | 0.322 | 0.086 | 76% | 49% | 13% | 1.59 | 1.02 | 0.26 |
| 21 | 0.476 | 0.252 | 0.078 | 73% | 39% | 12% | 1.51 | 0.80 | 0.24 |
| 28 | 0.450 | 0.184 | 0.074 | 69% | 28% | 11% | 1.43 | 0.58 | 0.22 |

Figure 12A:
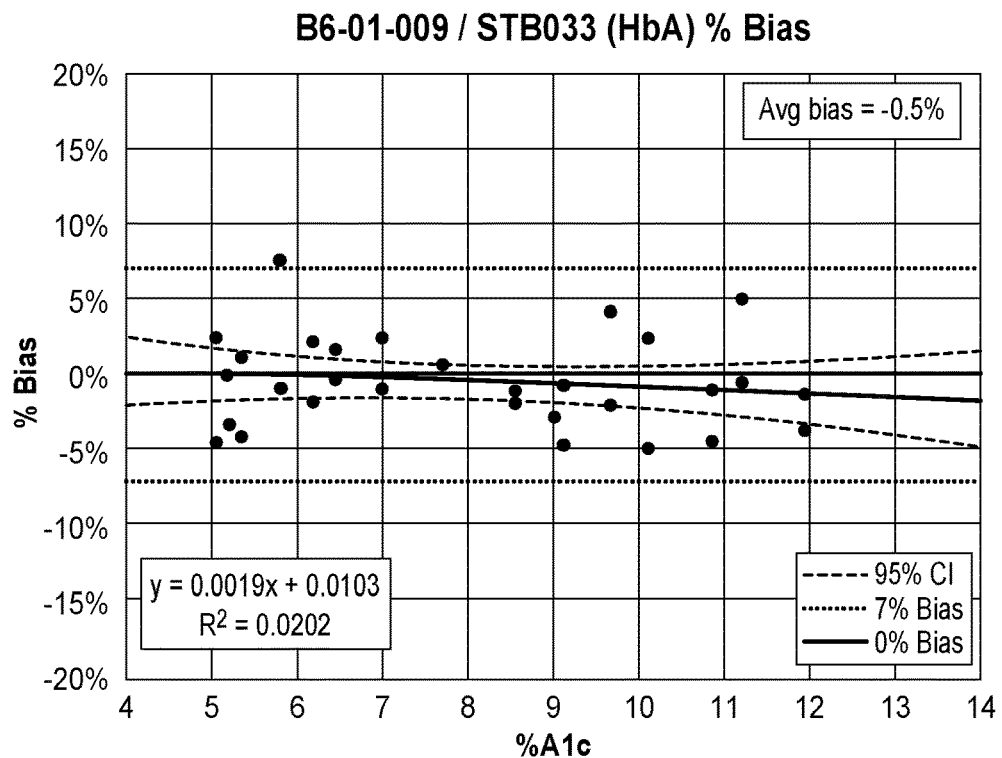
FIGS. 12A and 12B show graphs of variant bias for testing performed with two particular buffers STB, STB033 and STB065 for the HbA variant.
Figure 12B:
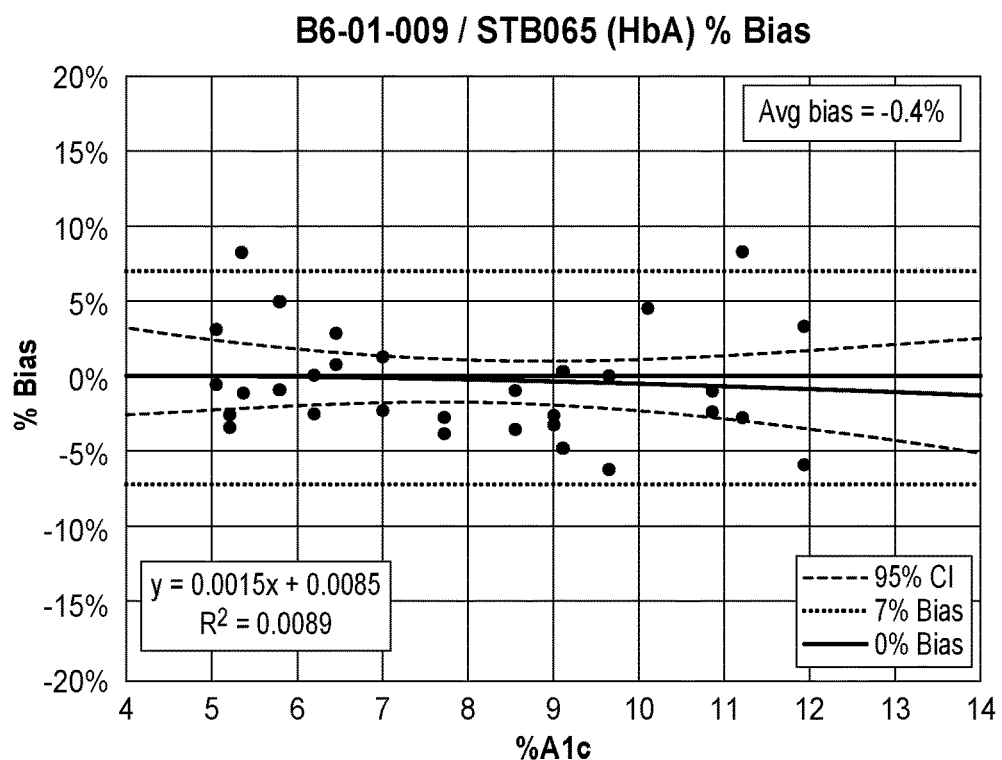
Figure 13A:
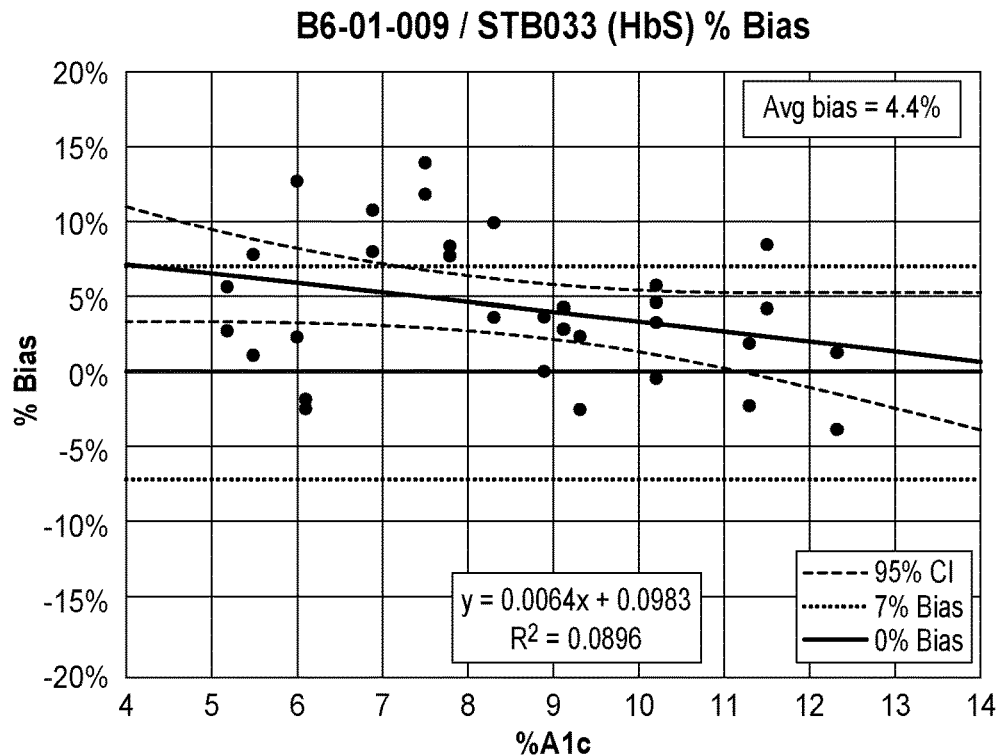
FIGS. 13A and 14B show graphs of variant bias for testing performed with three particular buffers STB, STB033, and STB065 for the HbS variant.
Figure 13B:
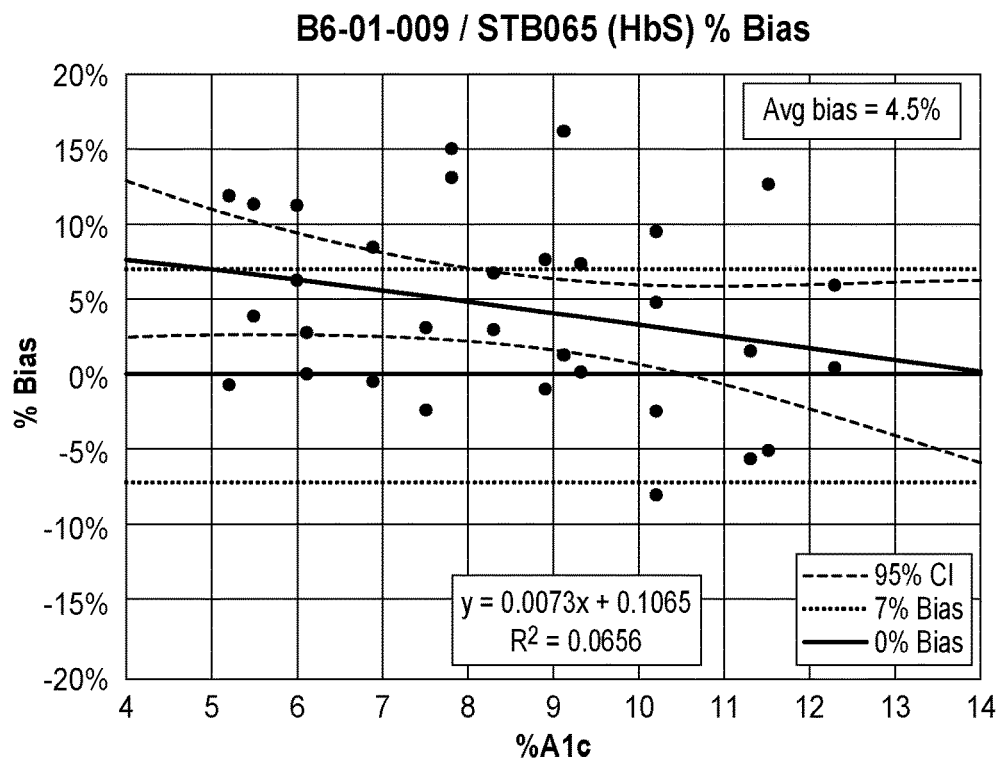
Figure 14A:
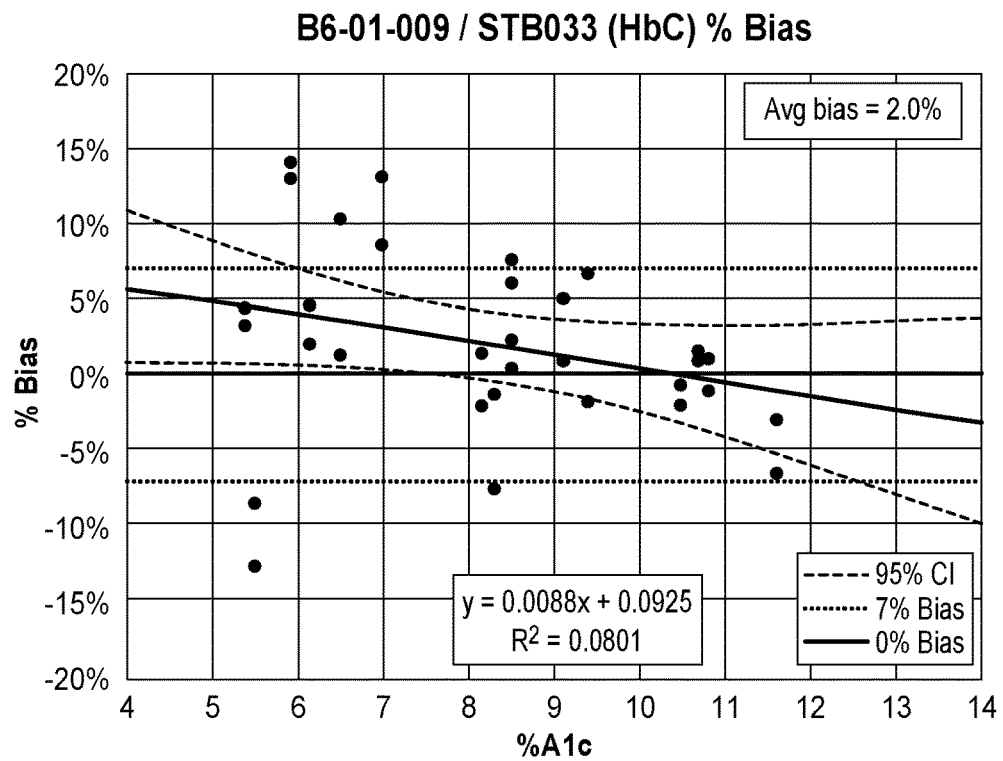
Figure 14B:
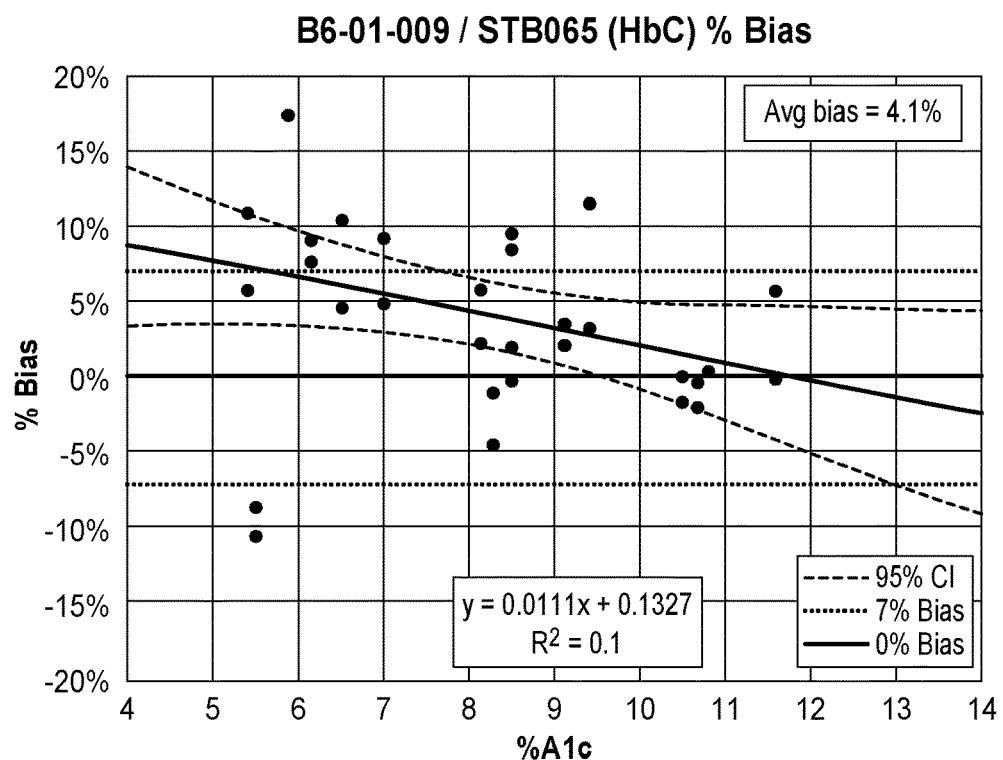

FIGS. 12A and 12B show graphs of variant bias for testing performed with three particular buffers STB, STB033, and STB065 for the HbA variant. FIGS. 13A and 13B show graphs of variant bias for testing performed with three particular buffers STB, STB033, and STB065 for the HbS variant. The goal is to have variant bias be within 7% or less. Tables 10 and 11 show results for variant bias and give the number of results that are outside of the 7% bias. FIGS. 14A and 14B show graphs of variant bias for testing performed with three particular buffers STB, STB033, and STB065 for the HbC variant. Tables 12 and 13 show results for variant bias and give the number of results that are outside of the 7% bias. Since the use of sodium perchlorate as an oxidizing agent shows similar results to the usage of $K_3Fe(CN)_6$, it may be substituted in and still similarly reduce the variant bias. The reason for substitution is that sodium perchlorate in many scenarios may provide enhanced stability to the STB when stored at room temperature.

TABLE 10

| | | Average bias & % bias for HbS | | | | | | | |
|---|---|---|---|---|---|---|---|---|---|
| | | Before the Correction | | | | After the Correction | | | |
| | STB | 4-7% 5 | 7-10% 6 | >10% 5 | Avg 16 | 4-7% 5 | 7-10% 6 | >10% 5 | Avg 16 |
| HbS % Bias | STB033 | 4.7% | 4.8% | 1.5% | 3.7% | 4.8% | 5.6% | 2.5% | 4.4% |
| | STB065 | 5.3% | 5.4% | 0.9% | 3.9% | 5.6% | 6.0% | 1.5% | 4.5% |

TABLE 11

| Count and % of sample outside 7% bias | | |
|---|---|---|
| HbS | STB033 | STB065 |
| Count | 10 | 12 |
| % | 31% | 38% |

TABLE 12

| | | Average bias & % bias for HbC | | | | | | | |
|---|---|---|---|---|---|---|---|---|---|
| | | Before the Correction | | | | After the Correction | | | |
| | STB | 4-7% 5 | 7-10% 6 | >10% 5 | Avg 16 | 4-7% 5 | 7-10% 6 | >10% 5 | Avg 16 |
| HbC % Bias | STB033 | 4.4% | 0.8% | -2.2% | 1.4% | 4.5% | 1.6% | -1.2% | 2.0% |
| | STB065 | 6.8% | 3.1% | -0.3% | 3.6% | 7.1% | 3.6% | 0.3% | 4.1% |

TABLE 13

| Count and % of sample outside 7% bias | | |
|---|---|---|
| HbC | STB033 | STB065 |
| Count | 9 | 12 |
| % | 31% | 38% |

Figure 15:
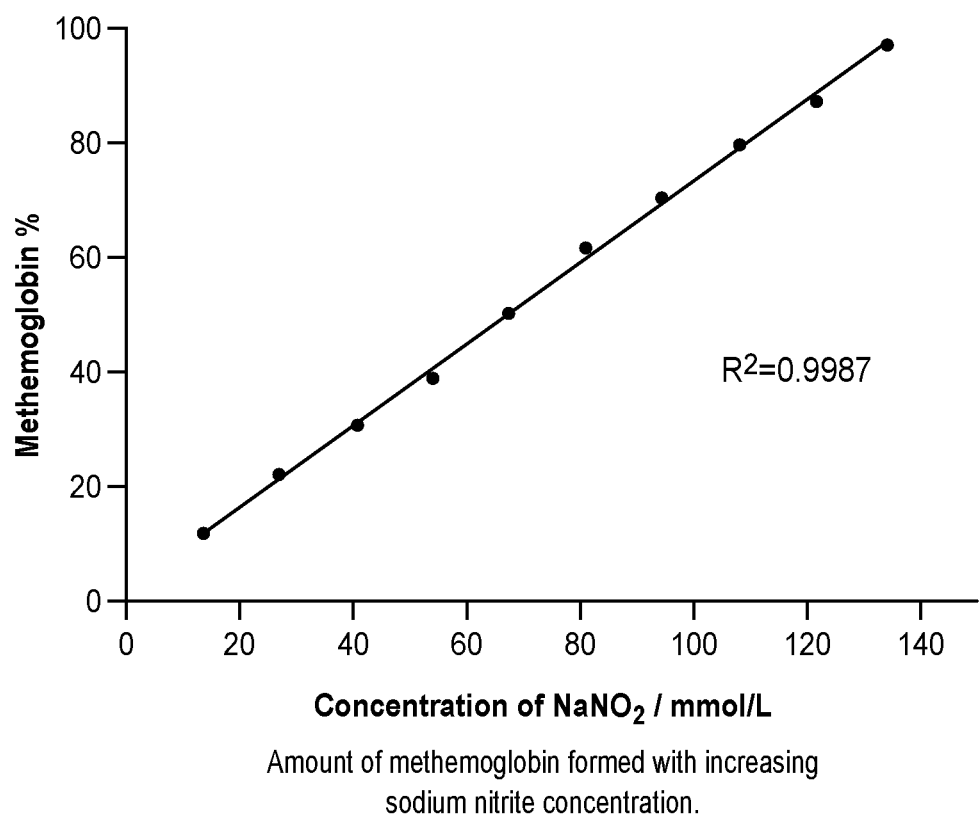
FIG. 15 shows an exemplary graph of the concentration of NaNO2 and the percentage of methemoglobin created from hemoglobin.

Additionally, in some embodiments, sodium nitrite may be used as an oxidizing agent. FIG. 15 shows an exemplary graph of the concentration of $NaNO_2$ and the percentage of methemoglobin created from hemoglobin. Therefore, in many embodiments, STB098 or similar STB may be used.

In the embodiments discussed, various optimizations may be conducted. The goal of many of the embodiments is to provide a more strongly denaturing STB while also providing a more strongly bound antibody-microparticle combination. In some configurations discussed, alternative oxidizing agents are provided for the STB in order to increase the shelf life of the product at room temperature.

Figure 16:
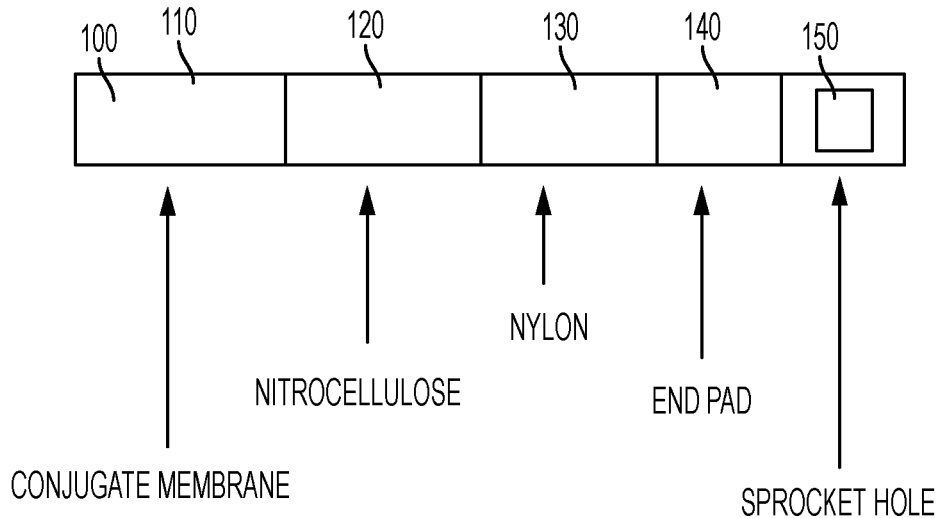
FIG. 16 shows one embodiment of the components of the lateral flow strip architecture.
Figure 17:
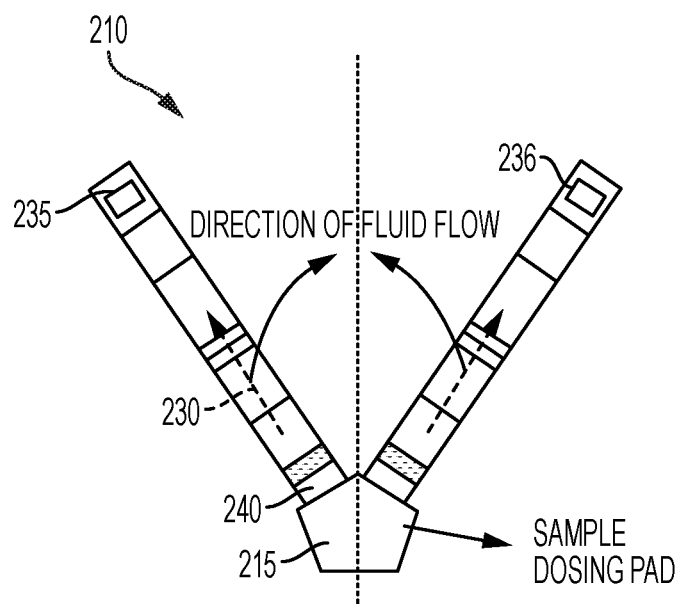
FIG. 17 shows an exemplary lateral flow test strip for use in the testing of hemoglobin.

FIG. 16 shows one embodiment of the components of the lateral flow strip architecture. This lateral flow strip architecture and that described in FIG. 17, as well as many others that may occur to one of ordinary skill in the art in light of this disclosure, may be used with the chemistries described herein. This architecture and the architecture of FIG. 17 are purely exemplary and many alternatives will occur to those skilled in the art. While methods of detecting hemoglobin and glycated HbA1C ("A1C") in whole blood may not be new, the particular agents and chemistries described herein for eliminating interference correction from hemoglobin variants are new and unique and their usage in various systems (including many lateral flow systems) for detecting hemoglobin and glycated HbA1C ("A1C") in whole blood are new and unique. In many embodiments, the systems and methods provide a point-of-care test to quantify the levels of hemoglobin and glycated HbA1C ("A1C") in whole blood. A lateral flow platform has been chosen to develop the lateral flow test. In this platform, a lateral flow strip (as shown in FIG. 1) usually consists of membranes which are coated with polystyrene particles coated with antibodies on the conjugate membrane portion while the antigen (protein conjugate) is coated on the nylon membrane portion of the lateral flow membrane. In one embodiment, the point-of-care test device employs a lateral flow methodology that does not use antibody-antigen interaction based detection. In this lateral flow method, the conjugate membrane, nitrocellulose membrane, and nylon membrane are layered in such a way as to obtain easy plasma/fluid flow, which enables the analytes to be captured on the membranes in different zones as shown in FIG. 1. FIG. 1 shows one embodiment of the components of the lateral flow strip architecture. FIG. 1 shows a lateral flow test strip 100. The lateral flow test strip 100 includes a conjugate membrane 110, a nitrocellulose membrane 120, a nylon membrane 130, and end pad 140, and a sprocket hole 150 for mounting the lateral flow test strip on a test strip holder, cartridge, or cassette.

In many embodiments, a hemoglobin lateral flow assay 210 may be created. The conjugate(s) described above will be coated on the area in zone 1 230 as shown in FIG. 17. The blue dyed particles will be coated with anti-hemoglobin antibodies at stripe 240. The system may include two arms 235, 236 and may include a sample dosing pad 215. It is certainly possible to only include a single arm; however, the redundancy may be used to prevent inaccuracies in measurements. Additionally, in many embodiments, one arm is used to determine total hemoglobin and the other is used to determine A1C. When a sample containing is dosed, the antibodies on the particles will bind to the hemoglobin in the sample. As the particles flow up the lateral flow membrane, the particles containing anti-hemoglobin antibodies (that are not bound with free hemoglobin) will bind to the hemoglobin on the conjugate membrane resulting in a response. When a very low concentration of hemoglobin is present, the particles will bind the conjugate striped in zone 1 230 the most. As the hemoglobin concentration in the sample increases, the particles with hemoglobin antibodies will bind the free hemoglobin and, as a result, the particles will not bind the conjugate in zone 1 230, leading to a higher reflectance. If the quantity of the hemoglobin is titrated from low to high, a dose response is obtained and thus enables the quantification of hemoglobin in the sample (and A1C).

Embodiments of systems and methods described herein provide for differentiation between glycated and unglycated hemoglobin (called "total hemoglobin" or "total Hb"). In many configurations, the glycated hemoglobin (A1C) is removed from the "total hemoglobin" via an affinity method (usually chromatographically; like boronate method); then that hemoglobin would result in a differentiated hemoglobin sample (called "differentiated hemoglobin" or "diff Hb") as expressed by the following equation 1:

$$\text{"diff Hb"} = \text{total Hb} - \text{glycated HbA1C} \tag{1}$$

Thus, if one can quantify the level of "differentiated hemoglobin (diff Hb)," then percent glycated Hb easily can be computed by equation 2:

$$\% \text{ glycated HbA1C} = [(\text{total Hb} - \text{diff-Hb})/\text{total Hb}] * 100 \tag{2}$$

In many embodiments, a premix step may be included. Typically, a sample is exposed to a premix step with a buffer solution (referred to as the sample treatment buffer). After a premix, the sample and buffer solution are applied to a test strip. The test strip includes an antibody-microparticle zone and a capture zone for capturing antibodies that have not reacted with the sample. Typically, after the lateral flow of the sample, the flow of the microparticles is measured using an optical meter.

While specific embodiments have been described in detail in the foregoing detailed description and illustrated in the accompanying drawings, it will be appreciated by those skilled in the art that various modifications and alternatives to those details could be developed in light of the overall teachings of the disclosure and the broad inventive concepts thereof. It is understood, therefore, that the scope of this disclosure is not limited to the particular examples and implementations disclosed herein but is intended to cover modifications within the spirit and scope thereof as defined by the appended claims and any and all equivalents thereof.

What is claimed as new and desired to be protected by Letters Patent of the United States is:

1. A system for determining a concentration of hemoglobin A1C, the system comprising:
    a first lateral flow test strip, the first lateral flow test strip providing for a percent of HbA1C concentration and providing for the total amount of hemoglobin, an antibody-microparticle stripe on the first lateral flow test strip;
    a conjugate stripe on the first lateral flow test strip; and
    a sample treatment buffer, wherein the sample treatment buffer is denaturing, antibodies in the antibody-microparticle strip are covalently bound to microparticles, the microparticles include an aldehyde group, and the sample treatment buffer includes sodium perchlorate as an oxidizing agent.

2. The system of claim 1, wherein the sample treatment buffer includes 50 mM Imidazole, pH 7.0, 1M LiSCN, 0.5M GuSCN, 1% Polyoxyethyleneglycol Dodecyl Ether, and 500 mM $NaClO_4$.

3. The system of claim 1, wherein the sample treatment buffer includes 50 mM Imidazole, pH 7.0, 1M LiSCN, 0.5M GuSCN, 1% Polyoxyethyleneglycol Dodecyl Ether and lithium perchlorate.

4. The system of claim 1, wherein the sample treatment buffer includes 50 mM Imidazole, pH 7.0, 1M LiSCN, 0.5M GuSCN, 1% Polyoxyethyleneglycol Dodecyl Ether and sodium nitrite.

5. The system of claim 1, wherein the sample treatment buffer includes 50 mM Imidazole, pH 7.0, 1M LiSCN, 0.5M GuSCN, 1% Polyoxyethyleneglycol Dodecyl Ether, and 2.0925 g/L $K_3Fe(CN)_6$.

6. The system of claim 1, wherein the sample treatment buffer includes 50 mM Imidazole, pH 7.0, 1.5M NaSCN, 0.5M GuSCN, 1% Polyoxyethyleneglycol Dodecyl Ether, and 2.0925 g/L $K_3Fe(CN)_6$.

7. The system of claim 1, wherein the sample treatment buffer includes 50 mM Imidazole, pH 7.0, 0.75M LiSCN, 0.75M NaSCN, 0.5M GuSCN, 1% Polyoxyethyleneglycol Dodecyl Ether, and 2.0925 g/L KFeCN.

8. The system of claim 1, further comprising:
a second lateral flow test strip, the second lateral flow test strip providing for a percent of HbA1C concentration and providing for the total amount of hemoglobin, an antibody-microparticle stripe on the second lateral flow test strip.

9. A system for determining a concentration of hemoglobin A1C, the system comprising:
a first lateral flow test strip, the first lateral flow test strip providing for a percent of HbA1C concentration and providing for the total amount of hemoglobin;
an antibody-microparticle stripe on the first lateral flow test strip;
a conjugate stripe on the first lateral flow test strip; and
a sample treatment buffer, wherein the sample treatment buffer is denaturing, and antibodies in the antibody-microparticle stripe are covalently bound to microparticles, and wherein the sample treatment buffer includes sodium perchlorate as an oxidizing agent.

10. The system of claim 9, wherein the microparticles include an aldehyde group.

11. The system of claim 9, wherein the sample treatment buffer includes 50 mM Imidazole, pH 7.0, 1M LiSCN, 0.5M GuSCN, 1% Polyoxyethyleneglycol Dodecyl Ether, and 500 mM $NaClO_4$.

12. The system of claim 9, wherein the antibody is monoclonal.

* * * * *